United States Patent
Tybrandt et al.

(10) Patent No.: US 9,080,970 B2
(45) Date of Patent: Jul. 14, 2015

(54) SELECTIVE ION TRANSPORT DEVICE

(75) Inventors: Klas Tybrandt, Linköping (SE); Magnus Berggren, Vreta Kloster (SE)

(73) Assignee: OBOE IPR AB, Linköping (SE)

( * ) Notice: Subject to any disclaimer, the term of this patent is extended or adjusted under 35 U.S.C. 154(b) by 71 days.

(21) Appl. No.: 13/264,010

(22) PCT Filed: Apr. 14, 2010

(86) PCT No.: PCT/EP2010/054899
§ 371 (c)(1),
(2), (4) Date: Oct. 12, 2011

(87) PCT Pub. No.: WO2010/119069
PCT Pub. Date: Oct. 21, 2010

(65) Prior Publication Data
US 2012/0031757 A1    Feb. 9, 2012

(30) Foreign Application Priority Data
Apr. 14, 2009   (WO) ................. PCT/EP2009/002723

(51) Int. Cl.
*B01D 43/00*   (2006.01)
*G01N 27/447*   (2006.01)
(Continued)

(52) U.S. Cl.
CPC ........ *G01N 27/447* (2013.01); *G01N 33/48707* (2013.01); *H01L 51/05* (2013.01); *H01L 51/10* (2013.01)

(58) Field of Classification Search
CPC .......... G01N 33/48707; G01N 33/487; G01N 27/447; H01L 51/05; H01N 51/10
USPC ................. 257/E51.029, 40, 253, 288, 379; 438/82; 204/605, 606, 627, 630, 634
See application file for complete search history.

(56) References Cited

U.S. PATENT DOCUMENTS 2,799,638 A * 7/1957 Roberts .................... 205/748
2,933,444 A * 4/1960 Bott ........................ 204/634
(Continued)

FOREIGN PATENT DOCUMENTS

EP    1786049 A1   5/2007
EP    1862799 A1   12/2007

OTHER PUBLICATIONS

Isaksson et al., Organic Electronics, 9, 2008, 303-309.*
(Continued)

*Primary Examiner* — Luan Van
*Assistant Examiner* — Steven Rosenwald
(74) *Attorney, Agent, or Firm* — Michael G. Johnston; Moore & Van Allen PLLC

(57) ABSTRACT

A device for controlled transport of ions is provided comprising an ion source element and an ion target element both conducting ions of a first class e.g. cations, and an ion selective element which conducts ions of a second class e.g. anions. The device further comprises a transport element, which receives ions from the ion source element and releases them to the ion target element in response to an electrochemical potential difference provided across the ion transport element. In use a first electrochemical potential is applied to the control element, which increases the concentration of ions of said second class, which increased concentration in turn increases the ion transport rate of ions of said first class in the ion transport element.

20 Claims, 15 Drawing Sheets

(51) Int. Cl.
   *H01L 51/05* (2006.01)
   *H01L 51/10* (2006.01)
   *G01N 33/487* (2006.01)

(56) References Cited

U.S. PATENT DOCUMENTS 3,657,106 A * 4/1972 Smith .......................... 204/634
5,615,764 A * 4/1997 Satoh .......................... 204/252
8,715,478 B2 * 5/2014 Berggren et al. ............ 204/600

OTHER PUBLICATIONS

Nilsson et al. (Adv. Mater. 2005, 17, No. 3, Feb. 10).*
Kim et al. (Electrophoresis 2009, 30, 1464-1469).*
Chun et al. (Lab Chip, first published online Mar. 11, 2008, 8, pp. 764-771).*
Karnik et al. (Nano Letters, vol. 5, No. 5 published online Mar. 31, 2005, pp. 943-948).*
Isaksson, Joakim et al, "Electronic Control of Ca2+ signalling in neuronal cells using and organic electric ion pump" Nature Materials, Nature Publishing Group, vol. 6, No. 9., Sep. 1, 2007, pp. 673-679.
Isaksson, Joakim et al, Electronically controlled pH gradients and proton oscillations, Organic Electronics, Elsevier, Amsterdam, NL, vol. 9, No. 3, Jun. 1, 2008, pp. 303-309.
Cohen, Edward and Gutoff, Edgar, Editors, Modern Coating and Drying Technology, 1992, VCH Publishers, Inc. pp. 1-21.
International Preliminary Report on Patentability; Oct. 27, 2011; issued in International Patent Application No. PCT/EP2010/054899.
International Search Report; Aug. 18, 2009; issued in International Patent Application No. PCT/EP209/002723.
International Search Report; Jun. 2, 2010; issued in International Patent Application No. PCT/EP2010/054899.

* cited by examiner

Fig 1a
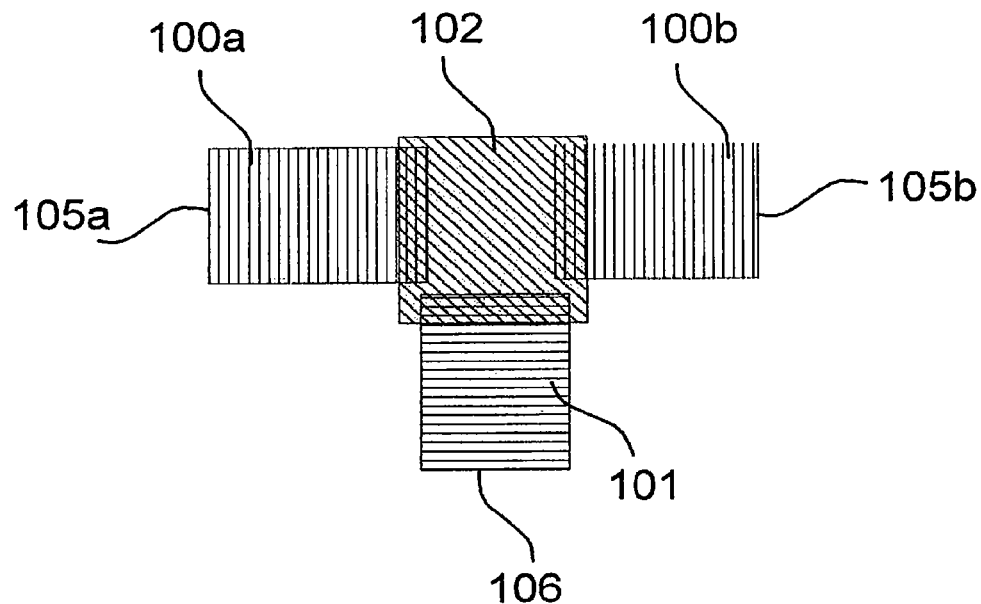
Fig. 1b
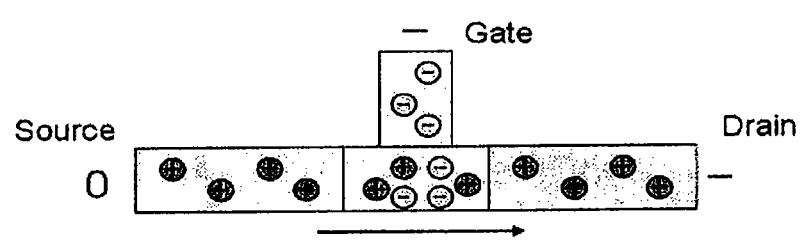
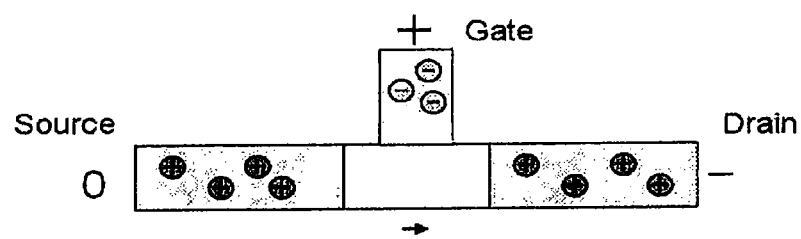

Fig 2f
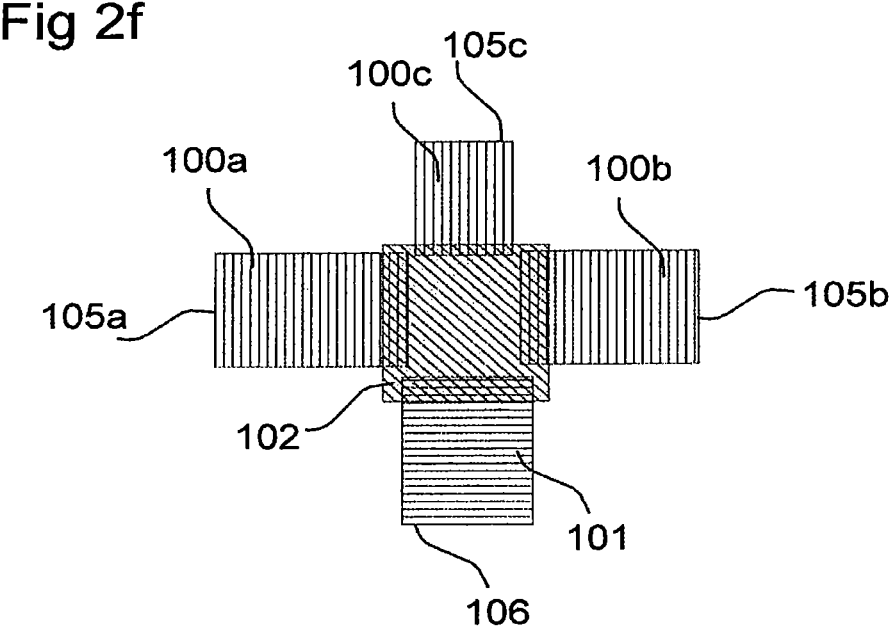
Fig 2g
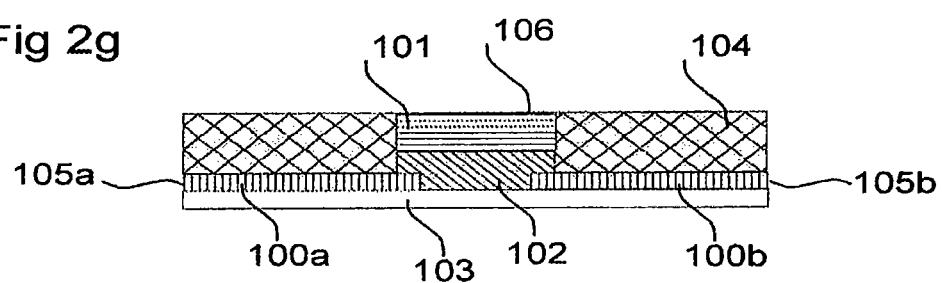
Fig 2h
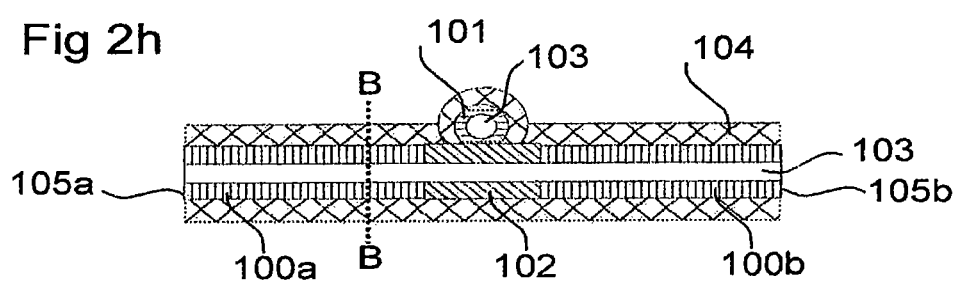
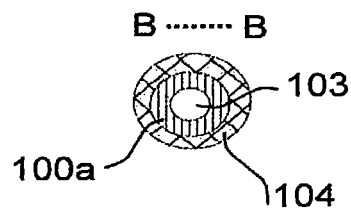

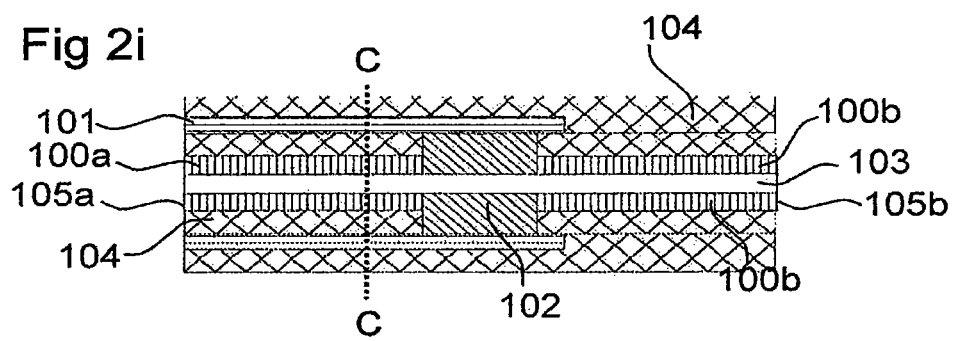
Fig 2i
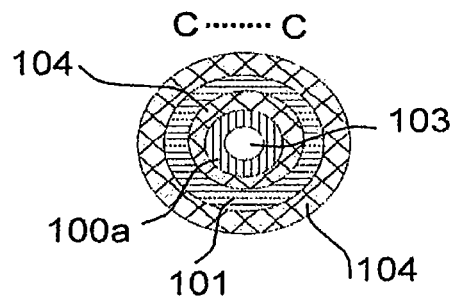
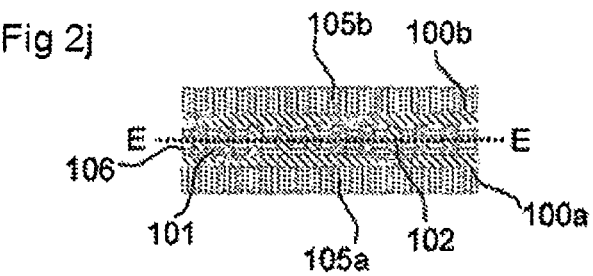
Fig 2j
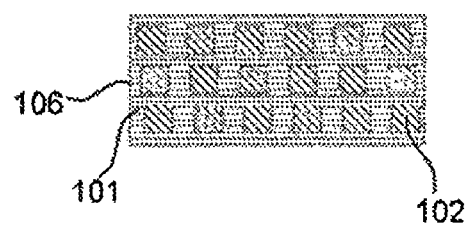

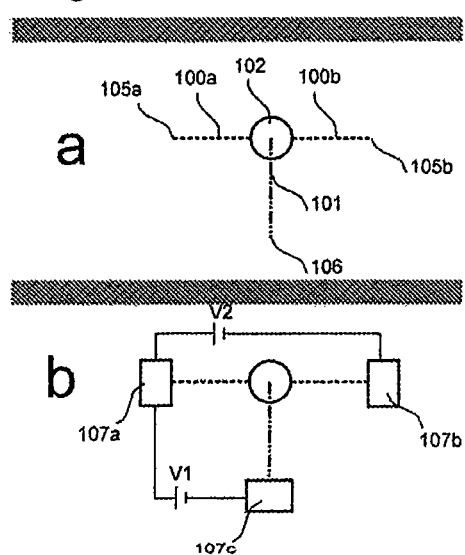

SELECTIVE ION TRANSPORT DEVICE

CROSS-REFERENCE TO RELATED APPLICATIONS

This application is filed under the provisions of 35 U.S.C. §371 and claims the benefit of International Patent Application No. PCT/EP2010/054899, filed on Apr. 14, 2010 entitled "SELECTIVE ION TRANSPORT DEVICE", which claims the benefit of priority of Patent Application No. PCT/EP2009/002723, filed on Apr. 14, 2009, each of which is hereby incorporated by reference herein in its entirety.

TECHNICAL FIELD

The present invention relates to a device for controlled transport of ions between a source element and a target element via an ion transport element, and to system comprising such devices arranged in series and/or parallel. The present invention further relates to use of such a device for transporting ions, as well as to methods of operating such a device.

BACKGROUND OF THE INVENTION

Ion signaling in eukaryotic cells is essential for numerous physiological processes, including regulation of exocytosis, contraction, gene transcription and fertilization, as well as maintenance of cell membrane potential. Ion signaling is equally important in prokaryotic cells, e.g. in osmoregulation. Ion signaling in cells may be affected by alteration of extracellular and intracellular concentration of ions. Such alterations result in intracellular concentration changes in the forms of i) rapid increase followed by a rapid decrease (termed spikes), ii) a sustained, elevated concentration, or iii) repetitive spikes that produce an oscillation of characteristic frequency and amplitude. Due to technical limitations of available methods to decipher these complex signaling pathways, very little is known about the molecular and physiological effects on cells. A limitation of certain concern is the inability of available methods to provide controlled ion fluxes to cells to be studied.

EP 1 862 799 discloses a devices for electrically controlled transport of ions between a source electrolyte and a target electrolyte, which device is capable of transporting ions of one or several ionic species from one or several source electrolytes to one or several target electrolytes, in which device the ion transport can be electrically controlled, and in which ions from one or several source electrolytes may be delivered to one or several target electrolytes in a space and time resolved manner. This device also provides for matrix addressing for delivery of ions.

SUMMARY OF THE INVENTION

An object of the present invention is to provide an ion transport device which is more easily extended to provide for a matrix addressing of a large number of channels, compared to e.g. the device described in EP 1 862 799.

This object is met by the invention as defined in the independent claims. Specific embodiments of the invention are defined in the dependent claims. In addition, the present invention has other advantages and features apparent from the description below.

According to a first aspect thereof, the invention relates to a device for controlled transport of ions comprising:
 a first source element arranged to receive ions of a first class from an ion source,
 a first target element arranged to release ions of said first class to an ion target, wherein each of said first source element and said first target element comprises an ion selective material,
 a first control element comprising ion selective material, which conducts a second class of ions,
 wherein said first class is one of cations and anions, and said second class is the other one of cations and anions,
 a first ion transport element arranged in direct ionic contact with all of said first source element, said first target element and said first control element,
 wherein said first control element, in use, is arranged to receive a first electrochemical potential which increases the concentration of ions of said second class in said ion transport element, and
 wherein said first ion transport element, in use, is further arranged to receive ions of said first class from said first source element in response to said increased concentration of ions of said second class, to release ions of said first class to said first target element, in response to a second electrochemical potential difference provided across said ion transport element and said first source element, and to provide an ionic connection for said ions of said first class between said first source element and said first target element.

In general, according to one embodiment said ion selective material conducts only the selected class of ions, at least when it is subjected to an electrochemical potential. In other words, said first target element is arranged to release ions of said first class to the ion target, wherein each of said first source element and said first target element comprises an ion selective material, which when subjected to an electrochemical potential only conducts said first class of ions. Further, said first control element comprises ion selective material, which when subjected to an electrochemical potential only conducts a second class of ions.

In relation to this invention the ion transport element comprises ion transport material.

In relation to this invention when an element comprises a specific material it may also consist of, or consist essentially of, this material. In other words, said first source material and/or said first target material and/or said first control material may consist of, or consist essentially of, e.g. a cation selective material. Said first source material and/or said first target material and/or said first control material may also consist of, or consist essentially of, an anion selective material.

In essence the invention resides essentially in that said first control element comprises the opposite class of material compared to said first source element and said first target element. I.e. when said first source and target element comprises cation selective material, said first control element comprises an anion selective material, and vice versa.

Below, examples will mainly be given with reference to a device for transport of cations between the source element and the target element. I.e. embodiment wherein said source element and said target element comprises cation selective material, and said control element comprises anion selective material. However, the given examples also provide a basis for providing a similar device for transport of anions between a source element and a target element, simply by exchanging the cation selective material for anion selective material and vice versa, as well as adjusting the applied electrochemical potential differences accordingly. When an electrical potential difference or electrical potential is used to achieve the desired electrochemical potential difference or electrochemical potential, the applied electrochemical potential is normally reversed in order to achive the desired electrochemical concentration.

In some examples reference is made to ions of a first class and ions of a second class. For a cation transport device, i.e. a device according to the invention wherein cations are transported at least from said source element to said target element, the ions of said first class are cations, and the ions of said second class are anions. For an anion transport device, i.e. a device according to the invention wherein anions are transported at least from said source element to said target element, the ions of said first class are anions, and the ions of said second class are cations.

In general, the transport of ions is normally effectuated of an electrochemical potential difference provided between said source element and said target element, e.g. by means of an electrochemical potential difference between a source electrolyte and a target electrolyte, wherein the source electrolyte is in ionic contact with said source element and the target electrolyte is in ionic contact with said target element. In some embodiments the electrochemical potential varies along the source element and/or the target element. Therefore, a respective point of reference may established, between which the electrochemical potential difference is determined. One of the points is e.g. located up stream of the ion transport element and the other point is e.g. located down stream.

The electrochemical potential of said source element refers to the electrochemical potential around 105a if not stated explicitly otherwise. The electrochemical potential of said target element refers to the electrochemical potential around 105b if not stated explicitly otherwise.

Generally, when it is stated that the electrochemical potential is altered, it is the absolute value of the electrochemical potential that is referred to. Generally, the electrochemical potential applied to said first control element is determined relative to said source element.

Below is in some instances a first (and a second) example described. Wherein properties of the first example is stated without parentheses, and the second example within parentheses.

The inventors have realised that, as the rate of e.g. anion (cation) transport between said source and target element, may be adjusted by the presence of cations (anions) in said ion transport material, this rate may be controlled by means of a control element provided to said ion transport material, which control element adjusts the concentration of cations (anions) in said ion transport material. I.e. when the electrochemical potential difference between said source and target elements is kept essentially constant, and the electrochemical potential provided to said control element is altered from a first predetermined value to a second predetermined value, the anion (cation) transport rate between the source element and said target element is increased, due to a higher concentration of cations (anions) in said transport element. In more detail, the increased concentration of ions effectuated by said control element, is according to one example almost momentarily compensated for by ions from said target element. Further, when the electrochemical potential provided to said control element is altered from said second predetermined value to said first predetermined value, the anion (cation) transport rate between the source element and said target element is decreased. In this way a control of the ion transport rate between said source element and said target element may be effectuated by means of an adjustment of the electrochemical potential applied to said control element.

According to one example, referring to an anion (cation) transport device, wherein anions (cations) are transported from said source element to said target element, the increased amount of cations (anions) in said ion transport material, which is compensated for by anion (cations) released from said source element, may be achieved by increase of the electrochemical potential applied to said first control element to a lager positive value, so that cations (anions) are released from said control element to said ion transport element. The cations (anions) ions may be provided from a cation (anion) source in ionic contact with said control element. By decreasing the applied electrochemical potential to a lower electrochemical potential the cations (anions) return to said control element, and the concentration of cations (anions) in said ion transport element is lowered. The compensating anions (cations) may return to an anion (cation) source in ionic contact with said source element. In this way the concentration of cations (anions), and hence the conductivity in the ion transport element, may be controlled.

Additionally or alternatively, in a cation transport device, the ion transport element may comprise fixed positive charges, and preferably an excess of fixed positive charges with mobile anions as counter ions. This is advantageous as it may suppress the leakage current between the source element and the target element in the off state or the less conductive state. This may be accomplished by lowering the concentration of mobile cations due to the fixed positive charges. In an anion transport device the ion transport may comprise fixed negative charges, and preferably an excess of fixed negative charges, having mobile cations as counter ions. This is advantageous as it may suppress the leakage current between the source element and the target element in the off state. This may be accomplished by lowering the concentration of mobile anions due to the fixed negative charges.

Additionally or alternatively, in a cation transport device, the ion transport element may comprise fixed negative charges, and preferably an excess of fixed negative charges with mobile cations as counter ions. This is advantageous as it may decrease the amount of anions needed from the control element. This may be accomplished by increasing the concentration of mobile cations due to the fixed negative charges. In a anion transport device, the ion transport element may comprise fixed positive charges, and preferably an excess of fixed positive charges with mobile anions as counter ions. This is advantageous as it may decrease the amount of cations needed from the control element. This may be accomplished by increasing the concentration of mobile anions due to the fixed positive charges.

A device wherein the increased conductivity of said ion transport element is provided by means of an injection of charges from said control element is described below.

According to this second aspect, a device is provided comprising a device for controlled transport of ions comprising:
 a first source element arranged to receive ions of a first class from an ion source, and
 a first target element arranged to release ions of said first class to an ion target, wherein each of said source element and said target element comprises an ion selective material, which conducts said first class of ions,
 a first control element comprising ion selective material, which conducts a second class of ions,
 wherein said first class is one of cations and anions, and said second class is the other one of cations and anions,
 a first ion transport element, which is:
 arranged to receive ions of said second class from said control element in response a first electrochemical potential difference provided across said ion transport element and said first control element, which received ions increases the concentration of ions of said second class in said first ion transport element at least until said applied potential difference is substantially altered;

arranged to receive ions of said first class from said first source element in response to said increased concentration of ions of said second class in said first ion transport element, to release ions of said first class to said first target element in response to a second electrochemical potential difference provided across said ion transport element and said source element, and to provide an ionic connection for ions of said first class between said first source element and said first target element; and arranged to release ions of said second class to said first control element in response to a third electrochemical potential difference provided across said ion transport element and said first control element, so as to enable a control of the transport of ions of said first class between said source element and said target element by means of an electrochemical potential applied across said first ion transport element and said first control element.

An arrangement for controlled ion transport comprising receptacles for receiving a respective source and target electrolyte is described below.

According to this third aspect, an arrangement is provided comprising:

an ion transport device in accordance with said first or second embodiment,
a source receptacle for receiving a source electrolyte,
a target receptacle for receiving a target electrolyte,
a control receptacle for receiving a control electrolye,
wherein said source and target electrolytes comprises ions of said first class, and said control electrolyte comprises ions of said second class,
wherein said first source element of said device is ionically connected to said source receptacle, said first target element of said device is connected to said target receptacle, and said first control element of said device is ionically connected to said control receptacle,
  a first electrochemical potential generator or means for providing a first electrochemical potential difference between said control receptacle and said ion transport element of said device for enabling transport of ions of said second class from said control receptacle to said transport element of said device,
  a second electrochemical potential generator or means for providing a second electrochemical potential difference between said source receptacle and said target receptacle for enabling transport of ions of said first class from said source receptacle to said target receptacle,
  a third electrochemical potential generator or means for providing a third electrochemical potential difference between said control receptacle and said ion transport element of said device for enabling transport of ions of said second class from said transport element to said control receptacle.

According to some embodiments, the means for providing an electrochemical potential difference between a first and a second element comprises a first electrode arranged to receive a predetermined electric potential and a first electrolyte, which electrolyte ionically connects said first electrode to said first element,
a second electrode arranged to receive a predetermined electric potential and a second electrolyte, which electrolyte ionically connects said second electrode to said second element,
wherein an electrochemical potential difference may be provided by said first and second element by providing a predetermined electric potential difference to said first and second electrodes.

According to some embodiments, the means for providing an electrochemical potential difference between a first and a second element comprises a third element of the same selectivity as said first element
a fourth element of the same selectivity as said second element wherein an electrochemical potential difference exist between said third element and said fourth element.

A system wherein two devices, arranged as described above are connected to each other in series is described below. This configuration may allow the channels to be controlled independently of each other.

According to this fourth aspect, a system is provided comprising the arrangement described in relation to said third aspect, and wherein said means for providing an electrochemical potential difference between a pair of elements selected from a group consisting of said first source element, said first target element and said first control element comprises a first electrode arranged to receive a predetermined electric potential, and
a first electrolyte, which electrolyte ionically connects said first electrode to a first one of said pair of elements,
a second electrode arranged to receive a predetermined electric potential, and
a second electrolyte, which electrolyte ionically connects said second electrode to a second one of said pair of elements,
wherein said electrochemical potential difference is applicable to said pair of elements by providing a predetermined electric potential difference to said first and second electrodes.

A system wherein two devices, arranged as described above are connected to each other in series is described below A system for controlled ion transport is provided comprising:

a first device in accordance with said first or second aspect,
a second device in accordance with said first or second aspect,
said first and second devices being arranged in series with each other, wherein an ionic connection is provided between the first target element of said first device and the first source element of said second device,
such that ions are transportable from the first source element of said first device via the ionic connection to the first target element of said second device,
at least after a first electrochemical potential difference has been provided between the control element and the ion transport element of first and second devices, respectively.

A system wherein two devices, arranged as described above are connected to each other in parallel is described below.

According to this fifth aspect, a system is provided comprising:

a first device in accordance said first or second aspect,
a second device in accordance said first or second aspect,
said arrangements being arranged in parallel with each other, wherein an ionic connection is provided between the first control element of said first device and the first control element of said second device,
such that ions may be transported via the ionic connection to said ion transport element of said first device and further to said ion transport element of said second device, at least after a first electrochemical potential difference has been provided between the common element and the ion transport element of said first and second devices, respectively.

According to some embodiments the ion source elements of a first and second device, each arranged in accordance to said first or second aspect, are two respective portions of a continuous sheet of material and/or the ion target elements of said of said first and second device are two respective portions of a continuous sheet of material.

In relation to this invention when a continuous sheet of material is discussed, reference is usually made to a material having an ion conductivity such that the electrochemical potential of at least two different predetermined positions in said material may be altered by introducing ions at normally only one predetermined position in said sheet.

A system for controlled ion transport wherein one receptacle for receiving a source electrolyte is shared between a the first source element of a first ion transport device and the first source element of a second ion transport device is described below.

According to this sixth aspect, a system is provided comprising:
　a first arrangement in accordance with said third aspect,
　a second arrangement in accordance with said third aspect,
　said arrangements being arranged in parallel with each other, wherein the source receptacle of said first arrangement and the source receptacle of said second arrangement are one and the same,
　such that an ion is transportable from the common source receptacle to either the target receptacle of said first arrangement or the target receptacle of said second arrangement, via either the ion transport element of said first arrangement or the ion transport element of said second arrangement.

In relation to this invention a common container may have two separated outlets, which are in contact with two separate element of a first and second device, respectively.

A system for controlled ion transport wherein one receptacle for receiving a target electrolyte is shared between the first target element of a first ion transport device and the first target element of a second ion transport device, is described below.

According to this seventh aspect, a system is provided comprising:
　a first arrangement in accordance with said third aspect,
　a second arrangement In accordance with said third aspect,
　said arrangements being arranged in parallel with each other, wherein the target receptacle of said first arrangement and the target receptacle of said second arrangement are one and the same,
　such that an ion is transportable either from the first source receptacle of said first arrangement or from the first source receptacle of said second arrangement to said common target receptacle, via either the ion transport element of said first arrangement or the ion transport element of said second arrangement, respectively.

Below is described a system comprising a first and second device for controlled ion transport, each arranged in accordance with said first or second aspect, wherein said first device is arranged for transporting ions of a first class (e.g. cations) between the source element and the target element thereof, and wherein said second device is arranged for transporting ions of a second class (e.g. anions) between the source element and the target element thereof. In other words, said first device is a cation (anion) transport device and said second device is an anion (cation) transport device, i.e. providing a pair of devices transporting cations and anions respectively.

According to this eighth aspect, a system is provided comprising:
　a first device in accordance with said first or second aspect,
　a second device for controlled ion transport comprising:
　　a first source element arranged to receive ions of said second class from an ion source, and
　　a first target element arranged to release ions of said second class to an ion target, wherein each of said source element and said target element comprises an ion selective material, which when subjected to an electrochemical potential only conducts said second class of ions,
　　a first control element comprising ion selective material, which when subjected to an electrochemical potential only conducts a first class of ions,
　　a first ion transport element arranged in direct ionic contact with all of said first source element, said first target element and said control element,
　wherein said first control element, in use, is arranged to receive a first electrochemical potential which increases the concentration of ions of said first class in said ion transport element, and
　wherein said first ion transport element, in use, is further arranged to receive ions of said second class from said source element in response to said increased concentration of ions of said first class, to release ions of said second class to said first target element, in response to a second electrochemical potential difference provided across said ion transport element and said source element, and to provide an ionic connection between said source and said target elements for ions of said second class,
　such that ions of said first class are transportable between said first source element and said first target element of said first device; and
　ions of said second class are transportable between said first source element and said first target element of said second device.

According to some embodiments, said pair of devices transporting cations and anions respectively, are arranged in parallel as described for two devices in relation to said fifth aspect.

According to some embodiments, said pair of devices transporting cations and anions respectively, has a common source receptacle and/or a common target receptacle as described for two ion transport devices in relation to said sixth and seventh aspect.

A system with a first and a second device each arranged in accordance with said first or second aspect, wherein a portion of the control element of the first device and a portion of the control element of the second device is one and the same, is described below. According to this ninth aspect, a system is provided comprising:
　a first device in accordance with said first or second aspect,
　A second device in accordance with said first or second aspect,
　arranged in parallel with each other, wherein a portion of the first control element of said first device and a portion of the first control element said second device are one and the same, which common control element portion is in ionic contact with both the ion transport element of said first device and the ion transport element of said second device,
　such that ions are transportable from the common control element portion to both the ion transport element of said first device and the ion transport element of said second device.

Below is described a system with a first and a second arrangement, each arranged in accordance with said third aspect, wherein the control receptacle of said first arrangement and the control receptacle of said second arrangement are one and the same. According to this tenth aspect, a system is provided comprising:

a first arrangement in accordance with said third aspect,
a second arrangement in accordance with said third aspect,
said arrangements being arranged in parallel with each other, wherein the control receptacle of said first arrangement and the control receptacle said second arrangement are one and the same, and
the control element of said first arrangement and the control element of said second arrangement are one and the same,
such that ions are transportable from the common control receptacle to the common control element and further to said ion transport element of said first device and thereafter to said ion transport element of said second device.

For a configuration arranged as described in relation to the ninth or tenth aspect, an opening of one channel or ion transport element at a time, with the advantage that for most cases fewer control elements are needed than the number of channels. This scheme becomes very useful when the number of channels is large, since n channels approximately require 2log2(n) control elements.

Below is described a matrix for controlled ion transport comprising at least two pair of devices, wherein each pair is arranged in series with each other, e.g. as described above, and wherein the two pairs of devices are arranged in parallel.

Below is described a method of operating a device as defined in any one of the aspects presented above. According to this twelfth aspect, a method is provided for operating a device as defined in any one of the above aspects to effect a controlled transport of ions. The method comprises:

providing a source electrolyte;
providing a target electrolyte;
bringing said first source element of the device in contact with the source electrolyte, and bringing the first target element of the device in contact with the target electrolyte;
providing a first control electrochemical potential between said source element and said target element of the device, and
providing a first transport electrochemical potential between said first control element and the ion transport element of said device to effectuate a change in the ion transport rate of said device.

An advantage related to any of the aspects presented above is that the ion transport rate between said source element and said target element is easily controllable by means of said control element. The use of a control element, instead of the potential difference between said source and target electrolytes, for controlling the ion transport rate, makes the body easily enlarged to comprise a large number of ionically separated ion transport elements, which are easily addressable.

In essence, the invention provides means to control the ion transport in a cation or anion selective channel by an ionic gate, and facilitates the arrangement of ionic circuits with addressing schemes similar to those found in electronics.

According to one example, the device may be used for spatially controlled drug release without any moving parts. Further, the invention enables ionic gating of the delivery of charged biosubstances which further provides electronic gating of multiple delivery spots in the ion transport devices. The invention may also be used e.g. for electrophoresis diagnostics, fuel cells, cleaning and separation etc.

Below are described different embodiments of the aspects presented above.

According to one example said first control element is arranged to receive ions of said second class from a control ion source, and
said first ion transport element is arranged to receive ions of said second class from said control element in response a first electrochemical potential difference provided across said ion transport element and said first control element, which received ions raises the concentration of ions of said second class in said first ion transport element at least until said applied potential difference is substantially altered, and
said second transport element is arranged to release ions of said second class to said first control element in response to a third electrochemical potential difference provided across said ion transport element and said control element, so as to enable a control of the transport of ions of said first class between said first source element and said target element by means of an electrochemical potential applied across said first ion transport element and said first control element.

This is an effective way of controlling the ion transport device.

According to one example, the ion transport element is arranged in ionic contact with said first source element, said first target element and said first control element, such that ions may be transported from said first source element to said first target element via said ion transport element, as well as exchanged between said control element and said ion transport element.

According to one example said first source element, said first target element and said control element are arranged as layers carried by a substrate, wherein said layers preferably are substantially parallel. This is advantageous as it facilitates the manufacturing of the device by means of e.g. printing techniques.

Further, the ion transport element may cover at least a respective portion of said first source element, said first target element and said control element, wherein the side of said first control element and the side of said first target element, which are covered by said ion transport element, both face in the same direction. In this way a lateral device may be achieved, which is advantageous as it provides a device which is easy to manufacture by means of printing techniques.

Alternatively, the ion transport element covers at least a respective portion of said first source element, said first target element and said control element, wherein the side of said first control element and the side of said first target element, which are covered by said ion transport element, face in opposite directions. In this way a vertical device may be achieved. This is advantageous as a device having this geometry may be easier to connect to other elements.

According to one example of a vertical design, the control element is smaller than the width of the ion transport element, i.e. the control element does not cover the whole of the ion transport element. This may result in a slower injection of charges in the ion transport material from said control element and a more even spread of the injected charges.

Alternatively, the control element covers the width of the ion transport element. This may result in a fast injection of charges from the control element, and also in an initially high concentration of salt or ions close to said source and target elements.

Alternatively, the control element extends outside the width of the ion transport element. This may facilitate the manufacturing as the exact position of the control element is now less critical.

According to one example the device is carried by a substrate.

According to one example, the dimensions of at least one of said elements are chosen so as to provide desirable impedance. The desirable impedance may be achieved by choosing suitable cross section and/or length of the element.

This may be advantageous since it may change the characteristics of the ion transport device. Low impedance may give higher current for an essentially fixed electrochemical potential difference between source element and target element. Also, low electrochemical potential may be needed to operate the control element when a low impedance source element and a high impedance target element are used. High electrochemical potential may be needed to operate the control element when a high impedance source element and a low impedance target element are used.

A system comprises at least a first and a second device, each having a vertical arrangement, and wherein the control element of said first device and the control element of said second device are two respective portions formed in a continuous layer or sheet of material.

According to this thirteenth aspect, a system is provided wherein the first control element of said first device and the first control element of said second device at least partially is one and the same, such that the ion transport element of said first device and the ion transport element of said second device are both connected to the same common control element.

According to one example the support is cylindrical or string shaped, said elements are concentrically arranged around said support; said first source element, ion transport element and said first target element are axially juxtaposed along said support; wherein said device further comprises isolative material, which is arranged along the string and ionically separates said first target element and/or said first source element from said first control element, which control element extends along said fiber, wherein said control element is preferably arranged radially outside said ion transport element as well as said first source element and/or said second source element, and wherein an encapsulation layer is provided radically outside of said said first source element, ion transport element, said first target element and said control element.

Said support may for example be a textile fiber or a polymer fiber like polyamide nylon, PET or PBT polyester, phenol-formaldehyde (PF), polyvinyl alcohol fiber (PVA), polyvinyl chloride fiber (PVC), polyolefins (PP and PE), aromatic polyamids, polyethylene (PE), polyurethane fiber. The fiber may also be fiberglass, fibers made of ceramics, insulated metal wires or natural fibers like cellulose fiber.

According to one example, said source element is spatially separated from said target element by means of an intermediate member, wherein said intermediate member preferably comprises at least a portion of said ion transport element.

Further, said control element may be spatially separated from both said source element and said target element by means of an intermediate 15 member, wherein said intermediate member preferably comprises said at least a portion of said ion transport element.

In relation to this invention one, two, three or four of said first source element, said first target element, said first control element and said ion transport element comprises a solid or semi-solid material, which are directly or indirectly attached to a support.

According to one embodiment, said ion transport material consists of a material selected from a group comprising: gels, polymers, membranes, fluids and combinations thereof.

Examples of polymer gels are polyacrylamide, polyvinylalcohol (PVA) and polyacrylonitrile (PAN), Poly(ethylene glycol) (PEG).

According to one embodiment said source element, said target element and/or said control element is porous. This is advantageous as it facilitates a large contact area between the respective element and the ion transport material, as the ion transport element may fill the cavities of the element.

According to one embodiment the contact area or interface between the source element, and transport element is within the range of about 1 $nm^2$ to 1 $cm^2$, or within the range of 1 $nm^2$ to about 1 $mm^2$, or within the range of 10 $nm^2$ to about 1 $mm^2$, or within the range of 1 $nm^2$ to about 0.1 $mm^2$, or within the range of 1 $\mu m^2$ to about 0.01 $mm^2$ According to one embodiment the contact area or interface between the target element, and transport element is within the range of about 1 $nm^2$ to 1 $cm^2$, or within the range of 1 $nm^2$ to about 1 $mm^2$, or within the range of 10 $nm^2$ to about 1 $mm^2$, or within the range of 1 $nm^2$ to about 0.1 $mm^2$, or within the range of 1 $\mu m^2$ to about 0.01 $mm^2$ According to one embodiment said source element, target element and said ion transport element all consist of the same material, and the cross sectional area of said ion transport element is substantially smaller than the cross sectional area of said source element.

This is advantageous as it facilitates the manufacturing of the device. According to some examples the cross sectional area is smaller than 200 $mm^2$, or smaller than 200 $\mu m^2$, or smaller than 200 $nm^2$ According to one example said ion transport element is a liquid and the device further comprises an ion transport receptacle, arranged to receive said ion transport element or ionically connect to said ion transport element, which receptacle is preferably sealed, except for providing an ionic connection to said control element and between said first source element and said first target element. The use of a liquid is advantageous as it may give a fast switch time of the device, because the ionic species usually have higher motilities in liquids than solid materials. According to one optional example, the ion transport receptacle or compartment comprises solid and/or semi-solid materials, produced e.g. by lamination.

According to one example at least one of said ion selective materials is selected from a group comprising electrochemically active material, which redox state is modifiable. In other words, the redox state of the electrochemical material may be modified by exposing said material to an electrochemical reaction, which either oxidizes or reduces the material. In response to this altered redox state the electronic conductivity of said material may change. This effect may be used to alter the concentration of ions in said ion transport material. The electrochemically active material may e.g. be an electrically conductive polymer material.

According to one example said device further comprises a second control element, arranged in ionic contact with and spatially separated from said first control element by means of said ion transport material. This is advantageous as it facilitates a direct control of the electrochemical potential difference between said first control element and said ion transport element. Thus, it also facilitates the control of the ion concentration in said ion transport material, with little dependence on the electrochemical potential provided at said source element and said target element.

According to one example, the gate is arranged excentrically with respect to said ion transport region. This may influence the electrochemical potential necessary to operate the control element and the result of such operation.

According to one example, both a cation transport device and an anion transport device are used in the same system.

Further, the target element of the cation transport device, may be connected to the control element of the anion transport device.

Still further, the target element of the anion transport device, may be connected to the control element of the cation transport device.

Furthermore, according to one example one or several anion transport devices and/or one or several cation transport devices and/or salt bridges are used to realize logical circuits.

Although ion isolative means and encapsulation means are advantageous, these means are usually not necessary for the device to be able to transport ions.

Advantageously, two crossing ion-conductive channels are separated by ionically isolating means, preferably arranged as a layer or a sheet covering at least a portion of said ion-conductive channel. In other words, a device comprising a matrix arrangement as described above, wherein a portion of said first ion conductive channel is sandwiched between a substrate and one of the additional ion conductive channels, further comprises ion isolative means separating two crossing ion conductive channels from each other.

According to one embodiment, the source electrolyte is in physical contact with only one of the source electrodes. This is particularly advantageous for embodiments having at least two source electrodes, and where it is desirable to be able to separately control the ion transport from each of the electrodes.

According to one example it is desired to transport ions from a common electrolyte first via a first source electrode and later via a second electrode. If the electrolyte covers both a first and a second source electrode, the application of a potential to said first electrode, to effectuate the first ion transport, creates a field in the electrolyte, due to the potential difference between the electrodes. Hence, the application of a potential to said first electrode might effectuate an ion transport also via said second electrode. This may be avoided by separating the electrolyte which is in contact with the first electrode, from the electrolyte which is in contact with said second electrode.

Generally, all terms used in the claims are to be interpreted according to their ordinary meaning in the technical field, unless explicitly defined otherwise herein. All references to "a/an/the [element, device, component, means, step, etc]" are to be interpreted openly as referring to at least one instance of said element, device, component, means, step, etc., unless explicitly stated otherwise. Other objectives, features and advantages of the present invention will appear from the following detailed disclosure, from the attached dependent claims as well as from the drawings Ion Selective Materials:

In relation to this invention the term ion selective material refers to a material having a higher selectivity for either cations or anions. The selectivity of a material typically comes from fixed electric charges in the material which are compensated by mobile ions of the opposite charge (counter-ions) and exclude mobile ions of the same charge (co-ions, excluded e.g. by Donnan exclusion). The fixed charges can be included in the membrane in several different ways, e.g. ions covalently bond to a matrix, ions immobilized in pour walls by absorption, bulky ions trapped in a matrix etc. In a cation selective material (often called cation-exchange membrane) the concentration of mobile cations is higher than the concentration of mobile anions. This typically gives rise to a higher conductivity of cations than anions. In an anion selective material (often called anion-exchange membrane) the concentration of mobile anions is higher than the concentration of mobile cations. This typically gives rise to a higher conductivity of anions than cations. The concentration of fixed charges in the selective material may depend on pH and/or ionic strength.

The selectivity of a material typically depends on the IEC (ion exchange capacity) which is measured in meq/(g dry membrane)=mmol/(g dry membrane) fixed charges. High IEC gives high selectivity and vice versa. The IEC is typically in the range of 0.5-3 meq/(g dry membrane) for commercially available exchange membranes. The selectivity of a membrane also depends on the ionic strength (concentration) of the electrolyte with which it is in contact. When the electrolyte concentration is as high as the IEC of the membrane the selectivity of the membrane is poor.

In the ion transport device it is advantageous to choose source element, target element and control element so they have high selectivity with respect to the electrolytes they interface. This typically means that the IEC of the material is at least 5 times higher than the electrolyte concentration (in molar).

In a preferable configuration the IEC of the material is at least 10 times higher than the electrolyte concentration (in molar).

According to one embodiment the IEC of the source element, target element and/or control element is within the range of about 0.01 mmol/(g dry membrane) to 5 mmol/(g dry membrane), or within the range of 0.1 mmol/(g dry membrane) to 5 mmol/(g dry membrane), or within the range of 0.5 mmol/(g dry membrane) to 5 mmol/(g dry membrane), or within the range of 0.5 mmol/(g dry membrane) to 3 mmol/(g dry membrane), or within the range of 0.1 mmol/(g dry membrane) to 1 mmol/(g dry membrane), or within the range of 0.5 mmol/(g dry membrane) to 2.5 mmol/(g dry membrane).

Example of an anion selective gel is crosslinked polydiallyldimethyl ammonium chloride (DADMAC).

Examples of anion selective membranes are: Aciplex A-192, Aciplex-501SB, Aciplex A201, Aciplex A221, Selemion AMV, Selemion ASV, Selemion DSV, FuMA-Tech FAS, FuMA-Tech FAB, FuMA-Tech FAN, FuMA-Tech FAA FuMA-Tech FAD, Ionics Inc AR103QDP, Ionics Inc AR204SZRA, Ionics Inc AR112-B, PCA Polymerchemie Altmeier PC 100, PCA Polymerchemie Altmeier D PC 200 D, PCA Polymerchemie Altmeier PC Acid 35, PCA Polymerchemie Altmeier PC Acid 70, PCA Polymerchemie Altmeier PC Acid 100, PCA Polymerchemie Altmeier PC-SA, Morgane ADP, Morgane AW Tokuyama Co Neosepta AM-1, Tokuyama Co Neosepta AM-3, Tokuyama Co Neosepta AMX, Tokuyama Co Neosepta AHA, Tokuyama Co Neosepta ACM Tianwei Membrane Co. TWEDG, Tianwei Membrane Co TWDDG, Tianwei Membrane Co TWAPB, Tianwei Membrane Co TWANS Example of a cation selective polymer is Poly(stryrenesulfonate) (PSS). Examples of cation selective membranes are Aciplex K-192, Aciplex-501SB, Selemion CMV, Nafion NF-112, Nafion NF-1135, Nafion NF-115, Nafion N-117, FuMA-Tech GmbH FKS, FuMA-Tech GmbH FKB, FuMA-Tech GmbH FK-40, FuMA-Tech GmbH FKD, Ionics Inc. CR61-CMP, Ionics Inc CR67-HMR, PCA Polymerchemie Altmeier PC-SK Solvay S.A., Morgane CDS Morgane CRA, Tokuyama Co. Neosepta CM-1, Tokuyama Co. Neosepta CM-2, Tokuyama Co. Neosepta CMX, Tianwei Membrane Co TWCED, Tianwei Membrane Co TWCDD, Tianwei Membrane Co TWCEDI The ion selectivity of the materials can be combined with other properties, e.g. porosity or that the material is electrochemically active, as long as these additional properties don't cancel out the ion selectivity. Typically big pore size is desirable since it allows transport of big ions through the material. However big pore size tends to reduce the selectivity of the material.

The ion selective materials may be solid, semi-solid or liquid. Examples of liquid materials may be polyelectrolytes.

Cation exchange membranes contain negatively charged groups, such as —SO3-, —COO—, —PO32—PO3H—, —C6H4O—, etc., fixed to the membrane backbone. Anion exchange membranes contain positively charged groups, such as —NH3+, —NRH2+, —NR2H+, —NR 3+, —PR3+, —SR2+, etc., fixed to the membrane backbone. In homogenous membranes charged groups are chemically bonded to the membrane matrix. In heterogeneous membranes charged groups are physically mixed with the membrane matrix. Most of the practical ion exchange membranes are composed of either hydrocarbon or fluorocarbon polymer films hosting the ionic groups. Charged groups can be incorporated in polyacrylamide gels by polymerization.

A list of commercially available ion exchange membranes can be found at Journal of Membrane Science 263 (2005) 1-29.

One group of anion selective materials is anion-exchange linear polymers which are insoluble in water. Examples:

A copolymer of a trialkylvinylbenzylammonium salt and a vinyl compound (e.g., styrene, vinyltoluene, acrylonitrile, etc.) insoluble in water. A linear aminated polymer such as a quaternary ammoniated polysulfone formed by chloromethylating a polymer such as polysulfone, polyphenylene oxide or polyether ether ketone followed by imparting thereto a quaternary ammonium group with a trialkylamine. A blend of a polysulfone and a polytrialkylvinylbenzylammonium salt.
Ions:

The term "ion" as used herein encompasses not only positively or negatively charged monovalent or multivalent ionic species of atomic elements, but also other molecular species carrying a net positive or negative charge. Hence, in an embodiment of the invention it is intended to transport charged biologically active molecules or macromolecules such as charged amino acids, neurotransmitters, DNA, DNA sequences/fragments or plasmids, proteins, vitamins, peptides or hormones. In one embodiment of the invention, the ions that may be transported are cations, for example protons or metal ions, such as potassium or calcium ions. In another embodiment of the invention the ions that may be transported are anions. The term ion also encompasses species that may be charged by setting a certain pH of the electrolyte solution or channel. The pH needed to charge these species may be calculated from the pKa of these molecules. The term ion also encompasses molecules which may be chemically modified to obtain a net charge, e.g. by attaching an ion to them.
Transport Material:

With reference to this invention, an ion transport material is defined as a material which may conduct both cations and anions, and which is normally less selective than previously mentioned anions or cation selective materials.

However, the ion transport material may still contain a lower concentration of fixed electric charges compared to said selective material. In this material the concentration of mobile ions and thus the ionic conductivity can typically be modulated. The transport material may be a material selected from a group comprising gels, hydrogels, polymers, membranes and porous material. The transport material may also be a liquid (e.g. water), which is normally located in a compartment or container, and preferably a sealed compartment or container, such that the transport material does not leak.

The transport material may also be a porous structure which can be filled/soaked with a solvent or liquid polymer. The concentration of fixed charges in the transport material may depend on pH and/or ionic strength.

According to one embodiment the transport material is chosen to be less selective than the source element, target element and control element. In one configuration the IEC of the transport material is less than 10% of the IEC of the source element, target element and control element. In one preferred configuration the IEC of the transport material is less than 1% of the IEC of the source element, target element and control element.

According to one embodiment the IEC of the transport material is within the range of about 0 0.1 /(g dry membrane), or within the range of 0 to about 0.01 mmol/(g dry membrane), or within the range of 0 to about 0.001 mmol/(g dry membrane), or within the range of 0 to about 0.0001 mmol/(g dry membrane), or within the range of 0 to about 0.00001 mmol/(g dry membrane), or within the range of 0 to about 0.000001 mmol/(g dry membrane), or within the range of 0.001 to about 0.1 mmol/(g dry membrane), or within the range of 0.0001 to about 0.01 mmol/(g dry membrane).

This is advantageous as in many embodiments both cations and anions are to be transported into and out of the ion transport element comprising ion transport material. A low IEC value facilitates the transport of both types of ions.
Electrochemically Active Material:

In relation to this invention the term electrochemically active material refers to a piece of a material comprising a material having a conductivity that can be electrochemically altered through changing of the redox state of said organic material. The electrochemically active material is usually in ionic contact with at least one electrode via an electrolyte. Examples of such electrochemically active materials include electrically conductive polymers, as will be described below, carbon and certain metal oxides, such as indium tin oxide (ITO), nickel oxide (NiO), manganese dioxide ($MnO_2$) and tungsten oxide ($WO_3$).
Insulation Material:

Insulation materials may be either electrically insulating, ionically insulating or both electrically and ionically insulating at the same time. The insulation material may or may not be photopatternable. They encompass/comprise polymers such as photo resists including SU-8, polyimide, different kinds of lacquer such as acrylic resin, evaporation of oxides such as $SiO_2$, or nitrides such as $Si_3N_4$, spin on glass, ceramics, lamination foils. The insulation material is preferably non-permeable to solvents (e.g. water).
Encapsulation Material:

In the present disclosure, reference is made to an encapsulation material. This material may be either electrically insulating, ionically insulating or both electrically and ionically insulating at the same time. The encapsulation material may or may not be photopatternable. They encompass/comprise polymers such as photo resists including SU-8, polyimide, different kinds of lacquer such as acrylic resin, evaporation of oxides such as $SiO_2$, or nitrides such as $Si_3N_4$, spin on glass, ceramics, lamination foils. The encapsulation material is preferably non-permeable to solvents (e.g. water).
Substrate:

The substrate onto which the ion transport may be arranged is preferably electrically and ionically insulating and may comprise rigid materials such as Si wafers with an insulating oxide (SiOx) or nitride layer ($Si_3N_4$), glass wafers such as pyrex wafers, glass substrates, such as microscope slides, plastic substrates such as PET, polystyrene, used in petridishes, and ceramics. The substrates may also be flexible such as plastic films, Orgacon films (both plastic and paper), or paper based materials. The substrate is preferably non-permeable to solvents (e.g. water).

Salt Bridge

Salt bridge is defined as a material with mobile cations and anions, typically in high concentration.

The devices which provide an electrochemical potential are e.g. elements which convert electric potentials (e.g. from power sources) into electrochemical potentials for ions. This may be an electrode (e.g. metal electrode) in an electrolyte. This electrode may according to some embodiments be electrochemically active in itself, e.g. conducting polymer electrodes.

Semi-Solid Material:

The term semi-solid material refers to a material, which at the temperatures at which it is used has a rigidity and viscosity intermediate between a solid and a liquid. Thus, the material is sufficiently rigid such that it does not flow or leak.

Further, particles/flakes in the bulk thereof are substantially immobilized by the high viscosity/rigidity of the material. In a preferred case, a semi-solid material has the proper rheological properties to allow for the ready application of it on a support as an integral sheet or in a pattern, for example by conventional printing methods. After deposition, the formulation of the material should preferably solidify upon evaporation of solvent or because of a chemical cross-linking reaction, brought about by additional chemical reagents or by physical effect, such as irradiation by ultraviolet, infrared or microwave radiation, cooling etc. The semi-solid or solidified material preferably comprises an aqueous or organic solvent-containing gel, such as gelatin or a polymeric gel.

Electrolyte:

The electrolyte for use with the device or method of the present invention should preferably be based on a solvent which permits ionic conduction in the electrolyte, i.e. which allows for the dissociation of ionic substances such as salts, acids, bases etc. The solvent and/or the ionic substance may contribute nucleophiles. Possible electrolytes for use in combination with the inventive device are solutions of salts, acids, bases, or other ion-releasing agents in solvents that support the dissociation of ionic species, thus allowing ionic conductivity. In applications where it is required, the electrolytes may comprise buffer solutions, such as buffer solutions suitable for use with living organisms or biomolecules, such as proteins. Examples of such buffers include NaHPO4 and sodium acetate. As other non-limiting examples of possible electrolytes, mention can be made of: aqueous solutions of potassium acetate, calcium acetate, NaCl, Na2SO4, HCl, H3PO4, H2SO4, KCl, 5 RbNO3, NH4OH, CsOH, NaOH, KOH, H2O2; Ringer's solution, organic solvents such as acetonitrile, pyridine, DMSO, DMF, dichloromethane, etc., in combination with suitable salts, such as lithiumperchlorate and tertiary ammonium salts, e.g. tetra-butyl ammonium chloride; inorganic solvents such as hypercritical CO2, liquid SO2, liquid NH3, etc., in combination with salts that dissociate in these solvents; solvents displaying auto-dissociation, which results in the formation of ionic species, such as water, formic acid and acetic acid. The term electrolyte also encompasses solutions comprising charged biologically active molecules or macromolecules such as charged amino acids, DNA, DNA fragments and plasmids, proteins, vitamins, peptides or hormones. An electrolyte may also comprise cell culturing media or ingredients thereof, such as proteins, amino acids, vitamins, and growth factors. The electrolyte may also be in a semi-solid or solidified form, preferably comprising an aqueous or organic solvent-containing gel as described above. However, solid polymeric electrolytes are also contemplated and fall within the scope of the present invention. Furthermore, the term electrolytes also encompasses liquid electrolyte solutions soaked into, or in any other way hosted by, an appropriate matrix material, such as a paper, a fabric or a porous polymer. It also includes so called ionic liquids, which is liquids that contains essentially only ions. Examples of these are quarterial ammonium salts, phosphonium salts, mixtures of 1,3-dialkylimidazolium or 1-alkylpyridinium halides and trihalogenoaluminates, EMIM EtOSO3 (1-Ethyl-3-methylimidazolium ethylsulfate), LiClO4 dissolved in 1-butyl-3-methylimidazolium tetrafluoroborate [bmim][BF4].

Manufacturing

The ionic transistor device according to the invention is also particularly advantageous in that it can be easily realized on a support, such as polymer film. Thus, the different components can be deposited on the support by means of conventional printing techniques such as screen printing, offset printing, gravure printing, ink-jet printing and flexographic printing, or coating techniques such as knife coating, doctor blade coating, extrusion coating and curtain coating, such as described in "Modern Coating and Drying Technology" (1992), eds E D Cohen and E B Gutoff, VCH Publishers Inc, New York, N.Y., USA. In the embodiments of the invention that utilize a conductive polymer material in the electrodes and/or channel, this material can also be deposited through in situ polymerization by methods such as electropolymerization, UV-polymerization, thermal polymerization and chemical polymerization. As an alternative to these additive techniques for patterning of the components, it is also possible to use subtractive techniques, such as local destruction of material through chemical or gas etching, by mechanical means such as scratching, scoring, scraping or milling, or by any other subtractive methods known in the art. An aspect of the invention provides such processes for the manufacture of an ionic transistor device from the materials specified herein.

Thus, in one embodiment of the device, said electrodes and said channels are directly or indirectly attached to a solid support such as glass or to a flexible support such as polymer film.

The ionic transistor device according to the invention may preferably be encapsulated, in part or entirely, for protection of the device. The encapsulation retains any solvent needed for e.g. the liquid or solidified electrolyte to function. Encapsulation can be achieved through liquid phase processes. Thus, a liquid phase polymer or organic monomer can be deposited on the device using methods such as spray-coating, dip-coating or any of the conventional printing techniques listed above. After deposition, the encapsulant can be hardened for example by ultraviolet or infrared irradiation, by solvent evaporation, by cooling or through the use of a two-component system, such as an epoxy glue, where the components are mixed together directly prior to deposition. Alternatively, the encapsulation is achieved through lamination of a solid film onto the ion transport device. In preferred embodiments of the invention, in which the components of the ionic transistor device are arranged on a support, this support can function as the bottom encapsulant. In this case encapsulation is made more convenient in that only the top of the sheet needs to be covered with liquid phase encapsulant or laminated with solid film.

The inventive device may also be manufactured using conventional semiconductor processes, such as photolitography and etching. When such methods are used, the electrode material(s) may preferably be deposited onto the substrate using any suitable deposition method, e.g. printing or lamination. The substrate carrying the electrode material(s) may then be patterned using conventional photoresist/etching techniques, e.g. as described in greater detail in Preparatory Example 1 below. An ion-selective channel can be obtained e.g. by deposition of a suitable ion selective material.

BRIEF DESCRIPTION OF THE DRAWINGS

The above, as well as additional objects, features and advantages of the present invention, will be better understood through the following illustrative and non-limiting detailed description of preferred embodiments of the present invention, with reference to the appended drawings, wherein the same reference numerals are used for similar elements, and in which:

FIG. 1a schematically illustrates a top view of one embodiment of an ion transport device;

FIG. 1b schematically illustrates two respective side views of one example of a cation transport device, and examples of electrochemical potentials applied thereto when the device is in use;

FIGS. 2b-2e schematically illustrate side views, taken along the line A-A in FIG. 2a, of different configurations of the ion transport device illustrated in FIG. 2a;

FIG. 2f schematically illustrates a top view of one embodiment of an ion transport device, comprising two control elements;

FIG. 2g schematically illustrates a side view, taken along the line A-A in FIG. 2a, of a configurations of the ion transport device;

FIG. 2h schematically illustrates two cross-sectional views of an ion transport device wherein the support is string shaped or cylindrical, one of the cross-section is taken along the line B-B as illustrated in the other cross-section;

FIG. 2i schematically illustrates two cross-sectional views of an ion transport device wherein the support is string shaped or cylindrical. One of the cross-sections is taken along the line B-B as illustrated in the other cross-section;

FIG. 2j schematically illustrates two cross-sectional views of a matrix configuration of 6 by 3 ion transport devices. One of the cross-sections is taken along the line E-E as illustrated in the other cross-section; the figure schematically illustrates a system for controlled ion transport, wherein said ion transport element is arranged in apertures of said control element;

FIGS. 3a and b illustrate two schematic representations of an ion transport device;

FIG. 6b illustrates a schematic set-up of an arrangement as is illustrated in FIG. 6a;

FIG. 7a illustrates a schematic representation of several ion transport devices all transporting ions from a common source element;

FIG. 7b illustrates a schematic set-up of an arrangement as is illustrated in FIG. 7a;

DETAILED DESCRIPTIONS OF PREFERRED EMBODIMENTS

Figure 2A:
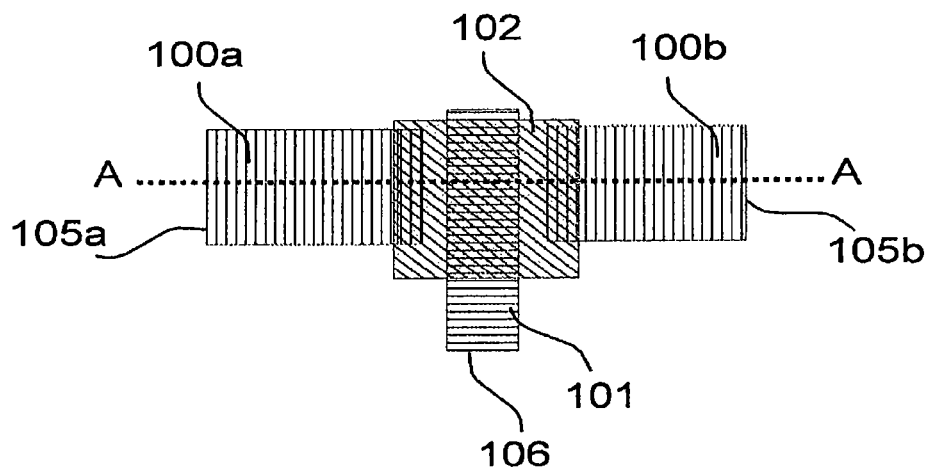
FIG. 2a schematically illustrates a top view of one embodiment of the invention.

In the below presented Figures the same or similar elements or members are denoted with the same reference numeral.

In general, the references denote the following:
100a is a source element
100b is a target element
101 is a control element (gate)
102 is a transport element
105a is an external interface to the source element
105b is the external interface to the target element
106 is the external interface to the control element
104 is encapsulation/insulation
103 is substrate/encapsulation/insulation
100c is the second control element
105c is the external interface to the second control element
107a,b, . . . are elements which translate electric potentials into electrochemical potentials. This is typically an electrode in contact with an electrolyte. In one configuration 107a,b, . . . are containers keeping electrolytes and electrodes. Typically 107a contains the ionic species to be transported in the device and 107b contains the target solution, which might be cell medium when the device is utilized to transport biomolecules to cell cultures cultured in 107b. 107c,d, . . . typically contain some inert electrolyte without specific function except modulating the ion conductivity of 102.

In one configuration illustrated in FIG. 1a, the ion transport device comprises two cation selective channels, or a first source element (100a) and first target element (100b) both arranged of cation selective element, are both in ionic contact with a transport region or ion transport element (102). An anion selective channel or first control element (101) is in ionic contact with the ion transport region 102. The respective channels or elements 100a, 100b and 101 may be in ionic contact with other media (e.g. channels, membranes, electrodes and/or electrolytes) at their external interfaces 105a, 105b and 106. The transport region (102) is in ionic contact with 100a, 100b and 101. In a preferred configuration the channels 100a, 100b and 101 are not in direct contact with each other. In one configuration the invention is encapsulated except at the interfaces 105a, 105b and 106. This encapsulation may consist of an encapsulating material or a combination of a substrate and an encapsulating material.

This device is operated by injection or extraction of ions through the external interfaces 105a, 105b and 106. Mainly cations may cross interfaces 105a and 105b while mainly anions may cross interface 106. When a difference in electrochemical potential exists between interfaces 105a and 105b ions may be transported between the interfaces. Since 100a and 100b are cation selective mainly cations will be transported. For a certain difference in electrochemical potential between interfaces 105a and 105b, the rate of which ions are transported depends on the ionic conductivity in the ion transport element or ion transport region 102. This ionic conductivity may be modulated depending on the electrochemical potential at the interface to the first control element 106. The first control element 106 may also be called gate in accordance with transistor terminology. When the electrochemical potential at 106 is such that anions in 101 are transported into 102, the anions are compensated by cations from 100a and/or 100b. This typically increases the salt concentration in 102 and thereby typically increases the ion conductivity of 102. When the electrochemical potential at 106 is such that anions in 101 are transported out from 102, cations are also transported out from 102 by 100a and/or 100b. This decreases the salt concentration in 102 and thereby typically decreases the ion conductivity of 102. When the electrochemical potential at 106 is such that the ion concentration in 102 is close to constant the ion conductivity of 102 is typically constant. Other effects like variations of the degree of hydration may be present in the materials 100a, 100b, 101 and 102 and affect the ion conductivity of the materials. In total the previously mentioned effects allows modulation of the ion flow between 105a and 105b by modulation of the electrochemical potential of 106. In the configuration above cations are mainly transported between 105a and 105b. Therefore this configuration is referred to as a cationic transistor or a cation transport device.

In FIG. 1a a lateral arrangement of the ion transport device is presented, wherein in the source element 100a, target element 100b, the control element 101 and ion transport element 102 all are arranged in parallel. The source element 100a, target element 100b and the control element 101 are preferably arranged in the same plane, and the control element covers all of the source element 100a, target element 100b and the control element 101, and provides an ionic contact with these three elements.

A schematic description of the device operation is given in FIG. 1b. In the on state the salt concentration in 102 is higher than in the off state. In this example the electrochemical potential is provided by means of a first second and third electrode, and a first, second and third electrolyte. Wherein each electrochemical potential is provided by providing suitable electrolytes and ionically connecting one of said electrodes via one of said electrolytes to a respective one of said source element, said target element and said control element. + stands for a higher electrical potential than 0 applied to the electrode, such that anions are fed to the control element. − stands for a lower electrical potential than 0, i.e. a negative potential. When a negative electrical potential is applied to the control electrode, anions are attracted to the control element. When a negative electrical potential is applied to the target electrode, and a higher potential is applied to the source electrode, cations are attracted to the target element from the source element. The cation transport rate between the source and the target element is dependent on the electrical potential applied to the control electrode. The length of the horizontal arrow indicates the rate of transported cations through the ion transport element in accordance with this embodiment.

In relation to all embodiments, the electro chemical potential of said source element refers to the electrochemical potential at the external interface of said source element 105a if not stated explicitly otherwise. The electrochemical potential of said target element refers to the electrochemical potential at the external interface of said target element 105b is not stated explicitly otherwise. Further, the electrochemical potential applied to said first control element is determined relative to said source element.

If 100a,b is replaced by an anion selective material, and 101 is replaced by a cation selective material the functionality of the device is maintained with the exception that mainly anions are transported between 105a and 105b and mainly cations are transported through 106, provided that also the polarity of the potential difference between the source element 100a and target element 100b as well as between the first control element 101 and the ion transport element 102 is adjusted. The possibility of modulating the ion conductivity in 102 by the electrochemical potential at 106 remains but the exact value of the electrochemical potential required to obtain a specific effect may change. Typically the same effect is obtained if the polarities of all connected power sources are switched. This configuration is referred to as an anionic transistor or anion transport device.

In the embodiments described in relation to the appended Figures the cationic transistor configuration is illustrated but the corresponding anionic transistor configuration may equally well be realised by the corresponding elements.

In the following section a number of non-limiting geometrical variations of the ion transport device are listed. They are views along the dashed line A-A in FIG. 2a. The basic working principle of the ion transport device is the same as described above but the device characteristics may depend on the exact geometry.

In FIG. 2a the ion transport device is arranged as described in relation to FIG. 1a, except that the gate 101 extends from one side of the ion transport element to the other side of the ion transport element in a direction orthogonal to the ion transport direction between the source element and the target element.

Figure 2B:
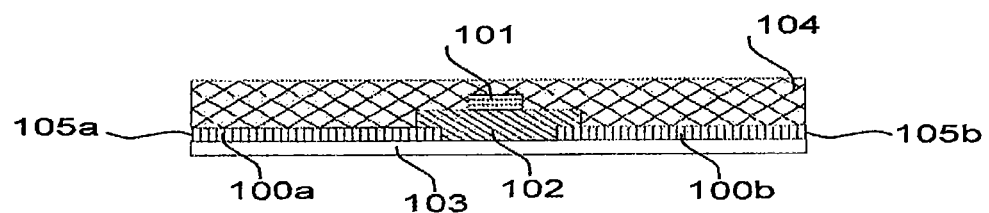

In FIG. 2b the control element is placed on top of 102 but do not cover the whole width of 102 in the ion transport direction. This may result in a slower injection of charge in 102 and an more even spread of the injected charges in 102.

Figure 2C:
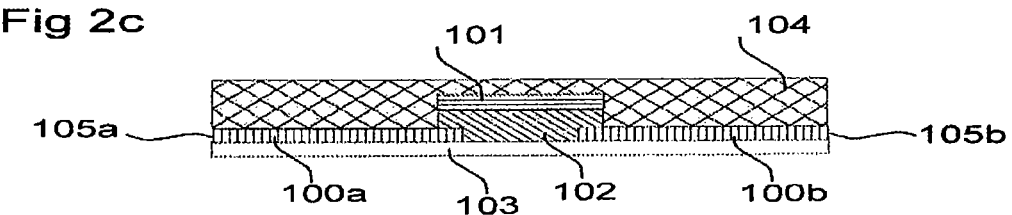

In FIG. 2c the gate 101 covers the whole width of 102 in the ion transport direction. This may result in fast charge injection but initially high concentration of salt close to 100a and/or 100b.

Figure 2D:
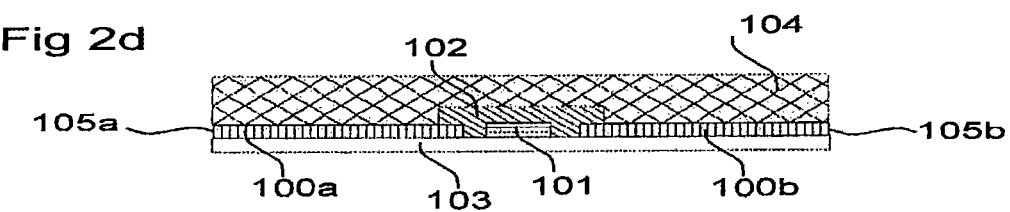

In FIG. 2d the gate 101 is placed on the substrate, as is the source element, target element and the control element. This may be a convenient way of realizing the invention if e.g. printing methods are utilized to fabricate the device.

Figure 2E:
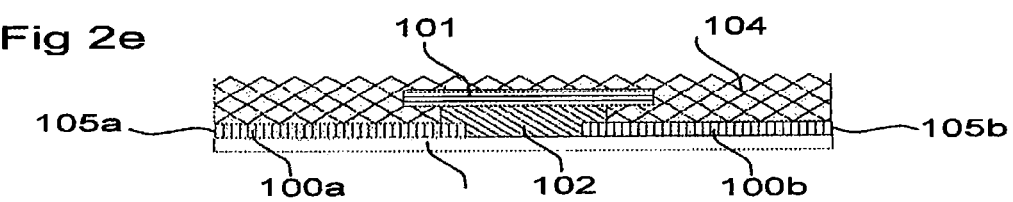

FIG. 2e, differs from FIG. 2d in that the gate 101 is arranged on top of the ion transport element, and covers more than the whole width of 102 in the ion transport direction. This may be convenient because this design does not depend on exact alignment of 101 if it is added after 102.

In FIGS. 2b, 2c, 2e and 2g a vertical ion transport device is provided, wherein the gate 101 has its interface 106 in the vertical direction. An advantage with this geometry may be that it is easier to connect other elements to 106.

In one configuration of the invention, gate 101 is not centered over the transport region. In other words, the control element is eccentrically located with respect to the ion transport element.

FIG. 2f shows a four-terminal configuration of the device. Compared to FIG. 1 an additional gate 100c has been added in contact with 102. In this configuration 106 and 105c are preferably connected to a separate electric circuit, apart from 105a and 105b. Then the electrochemical potentials at 106 and 105c may be regulated in a way to modulate the salt concentration in 102 with little dependence of the electrochemical potentials at 105a and 105b.

The geometry of the ion transport device is in no way limited to planar structures. Sometimes it may be advantageous to fabricate the invention in a cylindrical geometry, e.g. as a fiber or onto a fiber. For example it may be desirable to fabricate the invention into textiles. Another example is incorporation of the invention into tissue where a solid planar structure may cause unwanted effects on the tissue. FIG. 2h shows a configuration of the ion transport device where 100a, 100b and 102 are placed sequentially around or in axial juxtaposition along one fiber, while 101 is placed on or around another fiber and in ionic contact with 102 of the first fiber. In a preferred configuration the whole arrangement is encapsulated except the interfaces 105a, 105b and 106.

In another configuration shown in FIG. 2i the gate 101 is placed on the same fiber as 100a, 100b and 102 but with an insulating layer 104 in between 100a, 100b and 101. 101 is in ionic contact with 102.

FIG. 2j shows a vertical configuration of the ion transport device. 101 has the interface 106 on the side. 101 is patterned and have small holes in which 102 penetrates through. A first source element 100a and a first target element 100b are arranged in parallel, such that they face each other. A first control element 101, comprising apertures, is arranged between said source and target element. An ion transport 102 element is arranged in the apertures of the control element. Preferably, the control element is arranged such that when the electrochemical potential is altered in one end portion of the material, substantially the electrochemical potential in the whole of said ion transport element is altered. According to one embodiment the source element, target element and/or control element are/is arranged as continuous layers. This arrangement may give a large contact area between 101 and 102, and may result in a low leakage current in the off state. An advantage with this vertical structure may also be that large ionic currents may pass through it.

FIG. 3a shows a simplified way of illustrating the ion transport device. The representation does not show geometrical properties of the schemes (like distances) but shows how different parts are connected to each other.

According to one embodiment the distance between said source element and said target element is shorter than 1 m, shorter than 100 mm, shorter than 10 mm, shorter than 1 mm, shorter than 100 μm, shorter than 10 μm, shorter than 1 μm or shorter than 100 nm, shorter than 10 nm. According to one embodiment said distance is larger than 1 nm, 10 nm, or 100 nm, or 1 μm or 1 mm or 1 cm, or 10 cm, or 1 dm, or 1 m.

According to one embodiment the ion transporting length of said source element is shorter than 1 m, shorter than 100 mm, shorter than 10 mm, shorter than 1 mm, shorter than 100 μm, shorter than 10 μm, shorter than 1 pm or shorter than 100 nm, shorter than 10 nm. According to one embodiment said length is longer than 1 nm, or 10 nm, or 100 nm, or 1 μm or 1 mm or 1 cm.

FIG. 3b shows an addressing scheme of the invention. 107a,b,c are elements which translates electric potentials (e.g. from power sources) into electrochemical potentials for the channels. This is typically an electrode in an electrolyte. When an electrochemical potential is applied over 105a,b, cations are transported from the high potential towards the low potential. The transportation rate and thus the ionic current is affected by the concentration of mobile ions in the transport element 102 connecting the two channels 100a,b. The concentration of mobile ions in 102 can be modulated by the potential applied to 106. When the electrochemical potential at the interface 101/102 is lower than at the interface 100/102 cations will be injected from 100 and anions will be injected from 101 into 102. This will increase the concentration of mobile ions in 102 and thus increase the ionic current passing through the channels 100. When the electrochemical potential at the interface 101/102 is higher than at the interface 100/102 cations will be extracted through 100 and anions will be extracted through 101 from 102. This will decrease the concentration of mobile ions in 102 and thus decrease the ionic current passing through the channels 100. In a preferred configuration the ionic current through channels 100a,b can be controlled by a fixed gate potential due to the impedance of the channels 100a,b. Typically the current through V2 is stable when V1<V2/2 for a symmetric device.

Figure 4:
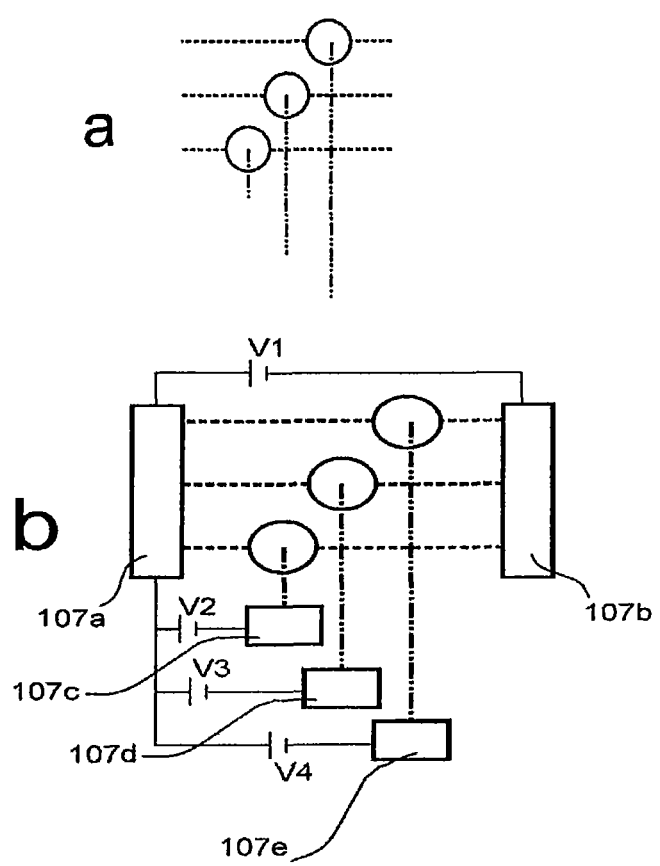
FIG. 4a illustrates a schematic representation of three ion transport devices connected in parallel.
FIG. 4b illustrates a schematic set-up of a arrangement comprising three ion transport elements arranged in parallel.

FIG. 4a shows an addressing scheme where three ion transport devices are arranged in parallel, and each channel or ion transport device is controlled by an individual gate 101. This configuration may allow the channels to be controlled independently of each other. FIG. 4b shows a specific implementation of FIG. 4a, wherein three ion transport devices are connected to a common source electrolyte and a common target electrolyte. The ion transport element of each device, is controllable by means of a separate ion control element, each arranged as described in relation to FIG. 3b.

Figure 5:
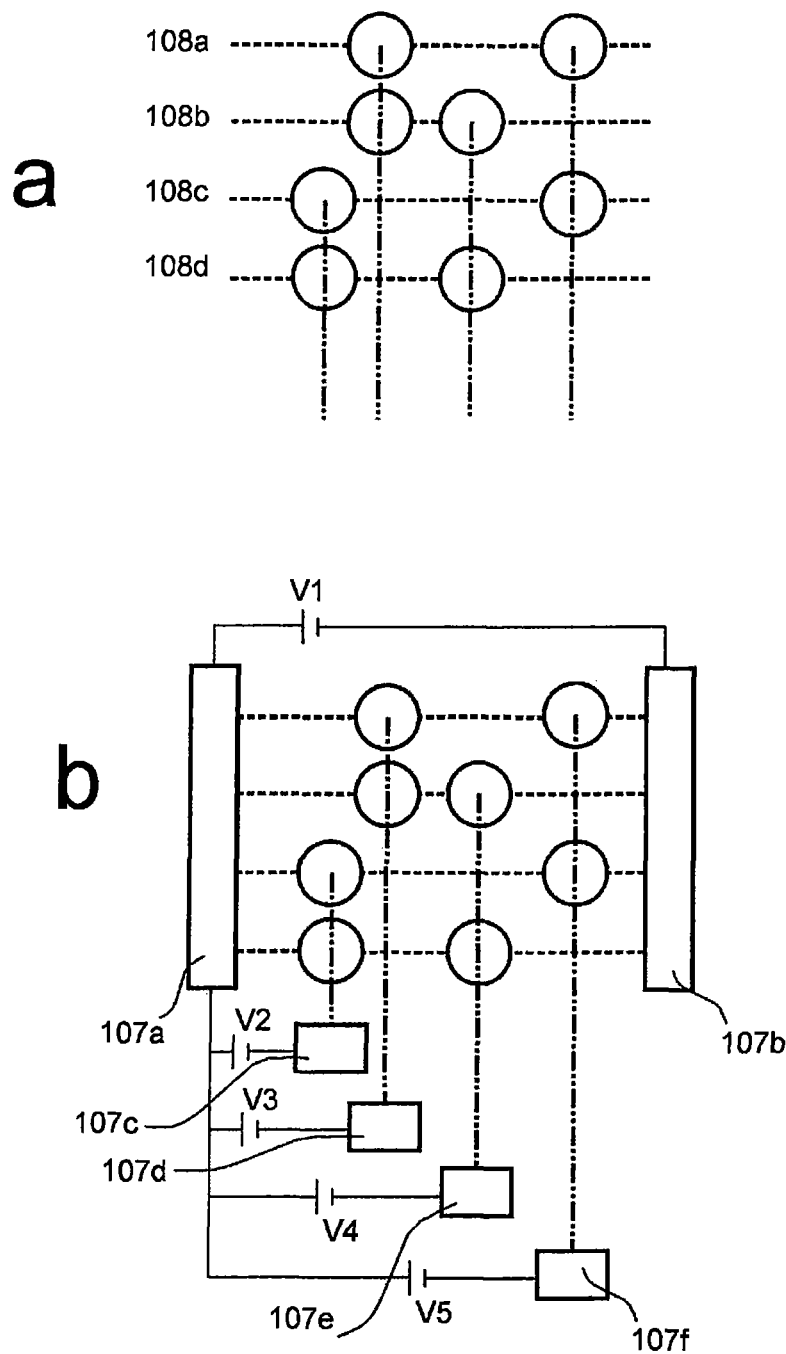
FIG. 5a illustrates two schematic representations of eight ion transport devices, connected in series two by two, wherein each pair of ion transport devices are arranged in parallel with the other pairs of ion transport devices. Further each ion transport element, in each pair, shares a control element with one ion transport device in another pair, such that all ion transport elements are connected two by two.
FIG. 5b illustrates a schematic set-up of an arrangement as is illustrated in FIG. 5a FIG. 6a illustrates a schematic representation of several ion transport devices all transporting ions to a common target element.

FIG. 5a shows an addressing scheme where each channel 108a,b,c,d contains two ion transport devices connected in series. Each gate or control element 101, illustrated by a vertical line, is connected to two ion transport materials 102. This allows one of the channels 108 to be opened while the others are closed, with the advantage that in most cases fewer gates 101 are needed than the number of channels 108. This scheme become very useful when the number of channels 108 increase since yy channels approximately require 2log2(yy) gates 101. The extrapolation of the addressing scheme may be obtained in the following way: choose the number of channels 108 to 2^x. Each channel should be assigned two ion transport devices at the same time as the 2^x gates 101 are assigned two ion transport devices from different channels 108.

FIG. 5b shows a specific implementation of FIG. 5a. The transport from 107a to 107b is driven by V1. V2-5 are connected to 107c-f and control the 8 ion transport devices in the scheme. When a predetermined pair of V2-5 are assigned positive voltages one corresponding channel 108 is opened. E.g. if V2>0, V4>0, V3<0 and V5<0 only the bottom channel 108d is open. The extrapolation to an arbitrary number of channels 108 is part of the embodiment, explained under FIG. 5a. This addressing scheme can be used to deliver ions from one or several electrolytes into one or several electrolytes. A non-limiting example is when cells are cultured in 107b and V2-5 are utilized to control which channel is open and thus where the delivery takes place. 108 may extend into 107b to release the ions at arbitrary locations. In other words, four pair of ion transport devices is provided, wherein the two ion transport devices in each pair are connected in series with each other, and the four pairs are arranged in parallel with each other. Connecting two ion transport devices in series mean that ions passes from the target element of the first device to the source element of the second device.

Figure 6:
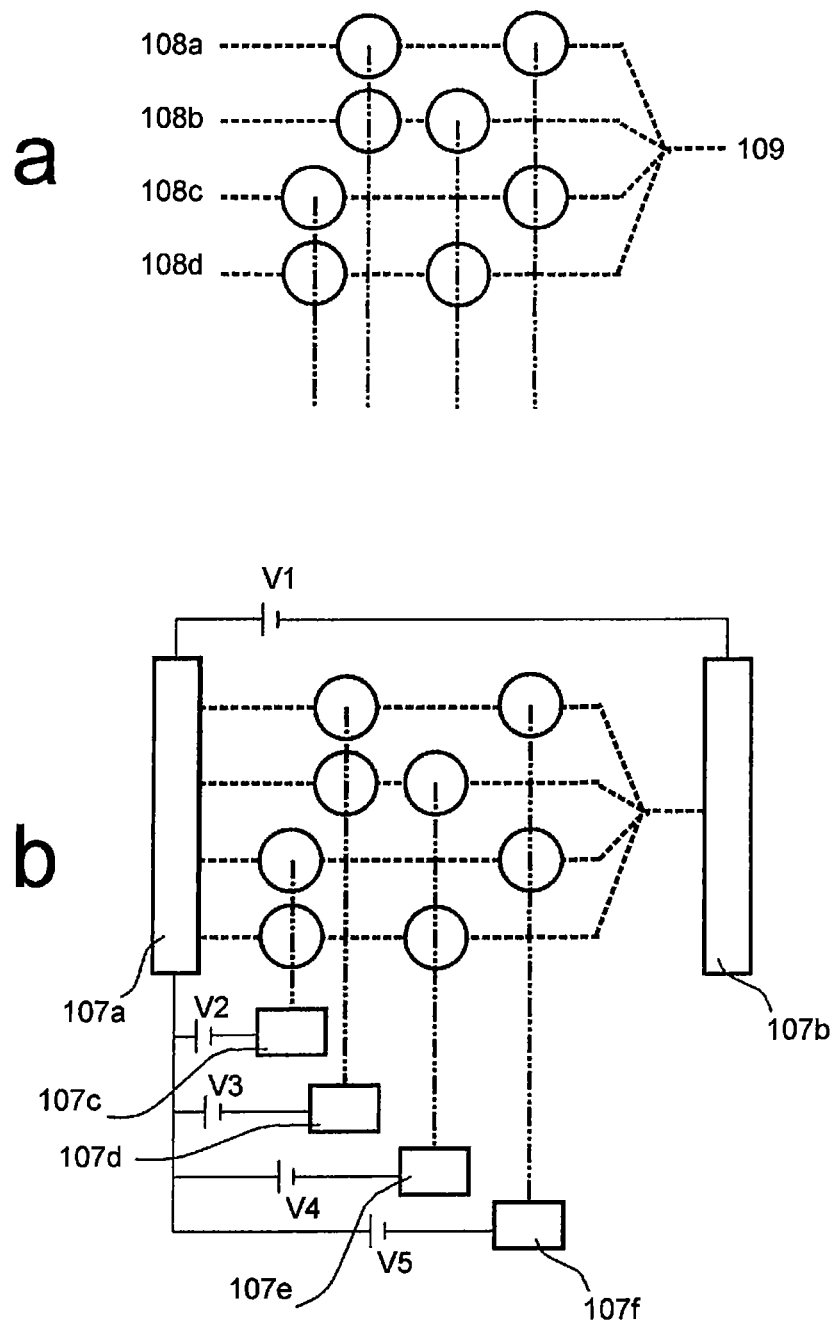

FIG. 6a shows an addressing scheme with functionality of a multiplexer, thus choosing one of 108a-d to go through to 109. The same basic principle of the addressing scheme is used as in FIG. 5a,b. FIG. 6b shows a specific implementation of FIG. 6a, wherein the down steam ion transport device in each pair are all connected to a common target element 109 and possibly a common target receptacle. The extrapolation to an arbitrary number of channels 108 is part of the embodiment.

Figure 7:
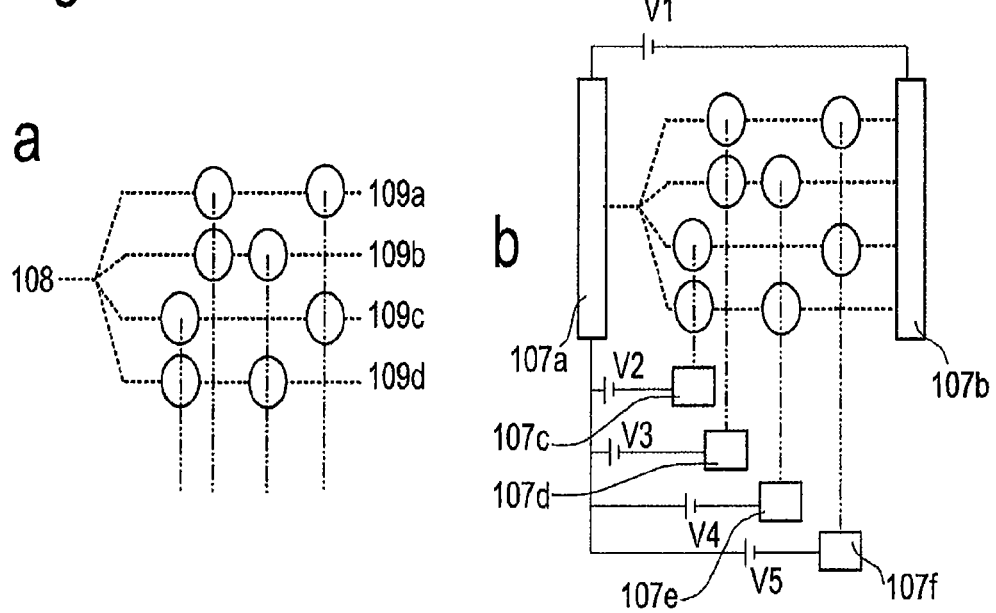

FIG. 7a shows an addressing scheme with functionality of a demux, thus choosing which one of 109a-d to let 108 go through. The same basic principle of the addressing scheme is used as in FIG. 5a, b. FIG. 7b shows a specific implementation of FIG. 7a wherein the up stream ion transport device in each pair are all connected to a common source element 109 and possibly a common source receptacle. The extrapolation to an arbitrary number of channels 100a,b is part of the embodiment.

Figure 8:
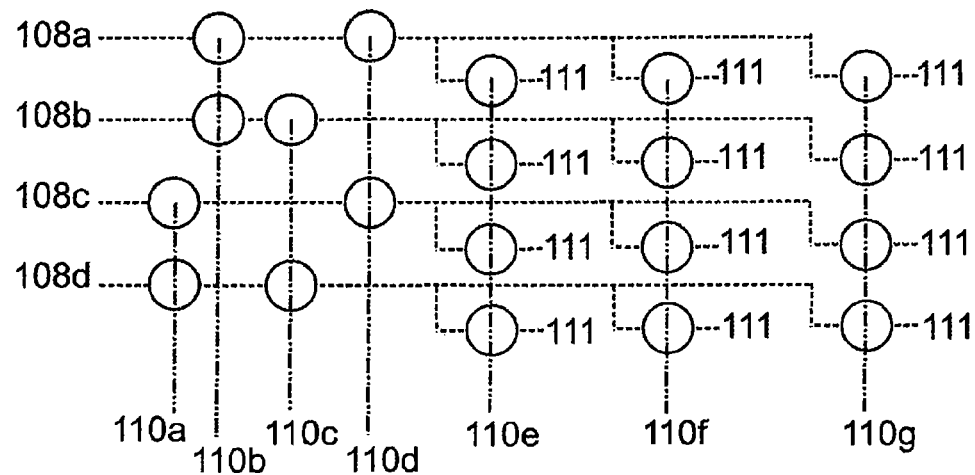
FIG. 8 illustrates a schematic representation of several ion transport devices having several delivery points.

FIG. 8 shows an addressing scheme for multiple delivery points 111. The delivery points 111 may be in ionic contact with an element 107b and 108a-b may be in contact with an element 107a. The addressing scheme consists of two steps. In the first step one of the channels 108a-d is opened by regulating gates 110a-d in the same way as in FIG. 5b. In the second step one of 110e-g is opened and the intersecting delivery point 111 of the one opened channel 108a-d and the one opened 110e-g is opened. The extrapolation to an arbitrary number of channels 108 is part of the embodiment and is done in the same way as described in relation to FIG. 5a. One advantage of the addressing scheme is that each channel 108 may give multiple delivery points 111 which still can be opened one by one. This may be a big advantage since the size might limit the number of channels 108, especially in a lateral structure.

According to one embodiment all 108 may be in contact with one element 107a which contain the desired ionic species to transport. All the delivery points 111 may be in contact with one element 107b which contains an electrolyte into which desired ionic species is transported. By applying a potential between 107a and 107b and operating the device as described above one of the delivery points 111 may be addressed at a time. The described system is an addressable matrix delivery system which might be used for controlled delivery of ions to cell cultures, to control chemical reactions in space and so on.

Figure 9:
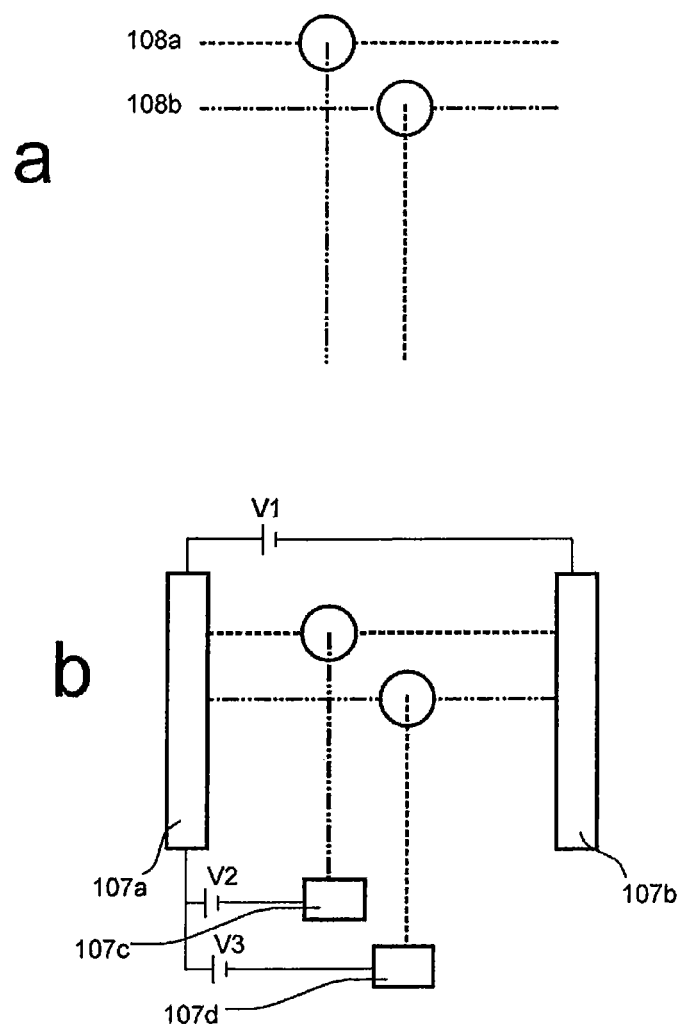
FIGS. 9a, b illustrate a schematic representation of an ion transport device, which allow for transport of both cations and anions through a respective channel.

FIG. 9 shows an addressing scheme in which anions or cations may be transported one at each time. In this embodiment a cation transport device and an anion transport device are connected in parallel, each device arranged as described above. In more detail said first ion transport device, the source element 100a and the target element comprises cation selective material, whereas the control element comprises anion selective material. The second ion transport device is arranged in the same way as the first ion transport device, except that in the second ion transport device the source element 100b and the target element comprises anion selective material, whereas the control element comprises cation selective material. The electrochemical potentials applied to the control element of the ion transport device, determine the type of ion which is transported. Cations are transported in when the following electrochemical potentials are applied $V1>0$ $V2>0$ $V3>V1$. Anions are transported when the following electrochemical potentials are applied $V1<0$ $V2<V1$ $V3<0$. So by switching the respective control element between an off and on state, the transport of cation and anions may be regulated.

In one embodiment of the invention, cation and anion selective channels are connected by a salt bridge. This salt bridge enables an ionic current to go between the two channels. In a preferred configuration the salt bridge has big capacity so it won't be consumed during the lifetime of the device.

In one embodiment of the invention, cationic transistors and/or anionic transistors and/or salt bridges are used in the same circuit.

In one embodiment of the invention, the channel of a cationic transistor or ion transport device, is connected to the gate of an anionic transistor or ion transport device.

In one embodiment of the invention, the channel of an anionic transistor or ion transport device is connected to the gate of a cationic transistor or ion transport device.

In one embodiment, the above described cation ion transport devices and/or anion ion transport devices and/or salt bridges are used to realize logical circuits.

In one embodiment of the ion transport device, the principal structure of FIG. 2f is used without potential difference between 105a and 105b. In this configuration the gates 101c and 106 control the diffusive flow of ions between the 105a and 105b.

In one embodiment of the ion transport device, addressing schemes as described in relation to FIGS. 3 to 9 may be used to deliver ions from a solution/electrolyte/gel/other medium into a solution/electrolyte/gel/other medium. Special cases of these are:

Delivery of ions to biological systems in vitro and/or in vivo.
Delivery of ions to regulate protein/DNA/macromolecule functionality (e.g. fibril formation).
Delivery of ions to cause/regulate chemical reactions.
Delivery of ions to trigger release of molecules/macromolecules from a responsive gel containing said molecules/macromolecules (e.g. pH sensitive gel like chitosan).
Delivery of ions to break a sealing of a compartment to trigger release of molecules/macromolecules.
In one embodiment the built up circuit is a logical circuit.
In one embodiment the built up circuit is a medical device.
In one embodiment ionic circuits are built up of biocompatible materials.

In one embodiment, circuits built up of ionic transistors are used to spatially regulate delivery in iontophoresis.

Figure 11A:
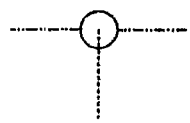
FIG. 11a illustrates schematically an anionic transistor with a cationic gate.
Figure 11B:
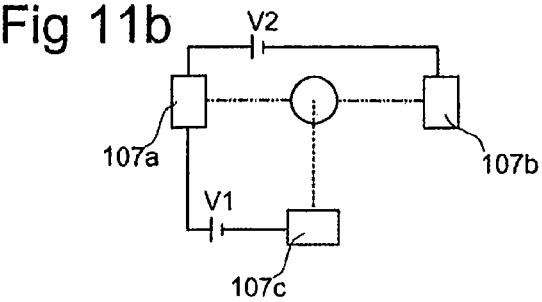
FIG. 11b illustrates schematically an addressing scheme of an anionic transistor.

FIG. 11a shows a schematic illustration of an anionic transistor with a cationic gate. FIG. 11b shows an addressing scheme of an anionic transistor. FIGS. 11a-11b show conversion elements 107a,b,c which translates electric potentials (e.g. from power sources) into electrochemical potentials for the channels. This is typically an electrode in an electrolyte. When an electrochemical potential is applied between source element interface 105a and target element interface 105b, anions are transported from the low electric potential towards the high electric potential. The transportation rate and thus the ionic current is affected by the concentration of mobile ions in the transport element 102 connecting the two channels 100a, b. The concentration of mobile ions in the transport element 102 can be modulated by the potential applied to the control element interface 106. When the electrochemical potential at the control element/transport element interface 101/102 is lower than at the source element/transport element interface 100a/102 anions will be injected from the source element 100a and cations will be injected from the control element 101 into the transport element 102. This will increase the concentration of mobile ions in the transport element 102 and thus increase the ionic current passing through the source and target elements 100a, 100b. When the electrochemical potential at the control element/transport element interface 101/

102 is higher than at the source element/transport element interface 100a/102 anions will be extracted through source and target elements 100a, 100b and cations will be extracted through the control element 101 from the transport element 102. This will decrease the concentration of mobile ions in the transport element 102 and thus decrease the ionic current passing through the source and target elements 100a, 100b. In a preferred configuration the ionic current through source and target elements 100a, 100b can be controlled by a fixed gate potential due to the impedance of the source and target elements 100a, 100b. Typically the current through V2 is stable when V1>V2/2 for a symmetric device.

Figure 11C:
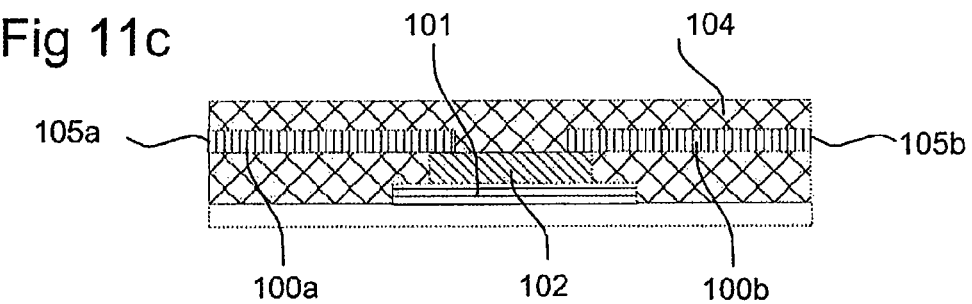
FIG. 11c illustrates a configuration of an anionic transistor with a bottom gate structure.

FIG. 11c shows a configuration of an anionic transistor with a bottom gate structure, fabricated in preparatory example 2.

Figure 12A:
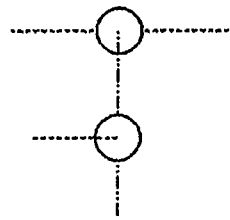
FIGS. 12a and 12b illustrate alternative addressing schemes.

FIG. 12a shows an addressing scheme where the drain of an anionic transistor is connected to the base of a cationic transistor. This configuration is advantageous since the cationic transistor is on only when both the gate and source of the anionic transistor are addressed in such a way that a negative current goes through drain of the anionic transistor.

Figure 12B:
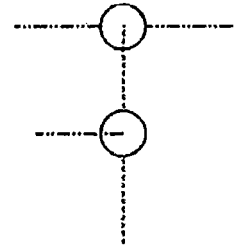

FIG. 12b shows an addressing scheme where the drain of a cationic transistor is connected to the base of an anionic transistor. This configuration is advantageous since the anionic transistor is on only when both the gate and source of the cationic transistor are addressed in such a way that a positive current goes through drain of the cationic transistor.

Figure 13A:
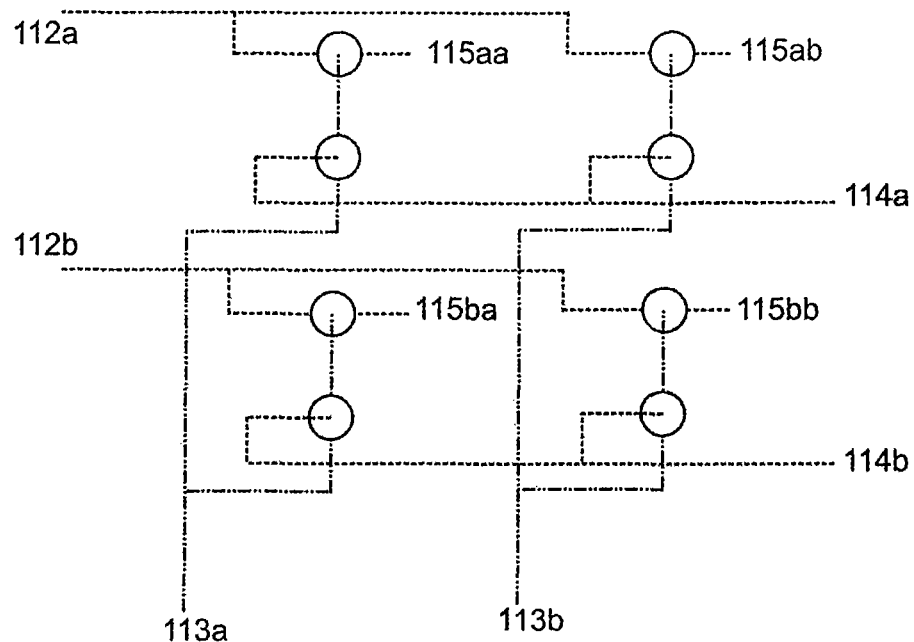
FIGS. 13a and 13b illustrate alternative matrix addressing scheme for multiple delivery points.

FIG. 13a shows a matrix addressing scheme for multiple delivery points 115 for cations. The delivery points 115 may be in ionic contact with a conversion element 107b and source channels 112a-b may be in ionic contact with an conversion element 107a. Each delivery point is addressed by two ionic transistors according to FIG. 12a. Delivery occurs through delivery point 115xy when both addressing channel 114x and addressing channel 113y are addressed is such a way that a positive current passes through delivery point 115xy. One advantage of the addressing scheme is that a specific delivery point 115xy can be individually opened for delivery while all other delivery points are closed. The extrapolation to an arbitrary number of delivery points 115 is part of the embodiment. The cationic and anionic channels are not in contact with each other, e.g. they may be in different layers with insulation in between. According to one embodiment all source channels 112 may be in contact with one conversion element 107a which contain the desired ionic species to transport. All the delivery points 115 may be in contact with one conversion element 107b which contains an electrolyte into which desired ionic species is transported. By applying a potential between conversion elements 107a and 107b and operating the device as described above one of the delivery points 115 may be addressed at a time. The described system is an addressable matrix delivery system which might be used for controlled delivery of ions to cell cultures, to control chemical reactions in space and so on.

Figure 13B:
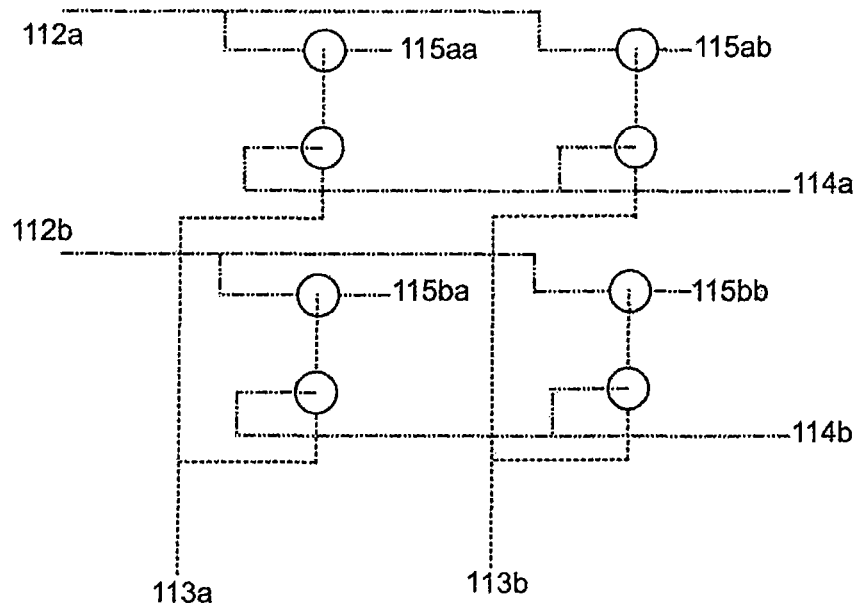

FIG. 13b shows a matrix addressing scheme for multiple delivery points 115 for anions. The delivery points 115 may be in ionic contact with a conversion element 107b and source channels 112a-b may be in ionic contact with a conversion 107a. Each delivery point is addressed by two ionic transistors according to FIG. 12b. Delivery occurs through delivery point 115xy when both addressing channel 114x and addressing channel 113y are addressed is such a way that a negative current passes through delivery point 115xy. One advantage of the addressing scheme is that a specific delivery point 115xy can be individually opened for delivery while all other delivery points are closed. The extrapolation to an arbitrary number of delivery points 115 is part of the embodiment. The cationic and anionic channels are separated from each other, e.g. they may be in different layers with insulation in between. According to one embodiment all source channels 112 may be in contact with one conversion element 107a which contain the desired ionic species to transport. All the delivery points 115 may be in contact with one conversion element 107b which contains an electrolyte into which desired ionic species is transported. By applying a potential between conversion elements 107a and 107b and operating the device as described above one of the delivery points 115 may be addressed at a time. The described system is an addressable matrix delivery system which might be used for controlled delivery of ions to cell cultures, to control chemical reactions in space and so on.

PREPARATORY EXAMPLE 1

General Procedure for Fabrication of the Ion Gated Ionic Transistor

A circuit according to FIG. 3b with an ionic transistor structure according to FIG. 2e was fabricated in a class 1000 cleanroom using photolithographic techniques and dry etching. In this example elements 107 consisted of PEDOT:PSS electrodes covered by SU8 with openings for electrolytes. A general procedure for fabrication of the ion transport devices is shown below. As substrate, an Orgacon foil (AGFA) was used. Orgacon is a laminate consisting of a first layer of a polyester base and a second layer of PEDOT:PSS.

The Orgacon foil substrate was cleaned by washing in acetone followed by washing in water. The substrate was then baked at 110° C. for 5 min in order to dry the substrate before the etch process step below.

The photoresist (S1818 Microposit) was spin coated onto the Orgacon foil substrate. The photoresist was exposed using a mask-aligner (Suss Microtech MA 6/BA 6). Development was done with a Microposit MF319 developer. The non-covered areas of PEDOT:PSS were etched away using a reactive ion plasma consisting of O2 and CF4. This created the basic pattern for the channels 100a,b and the electrodes which were part of 107. The non-etched photoresist was removed using a Microposit remover 1112A. Another layer of photoresist was patterned in order to create opening where PEDOT:PSS was to be over-oxidized to create the channels 100a,b. In the opening defined by the patterned photoresist, the PEDOT:PSS was exposed to 1% NaClO solution for 50 seconds. After rinsing in water the photoresist was removed using a Microposit remover 1112A. A layer of SU-8, acting as 104, (Microchem SU-8 2010) was spin-coated onto the patterned PEDOT:PSS. The SU-8 layer was baked by ramping the temperature from 50° C. to 110° C. during 16 minutes. The SU-8 layer was exposed using a mask-aligner (Suss Microtech MA 6/BA 6). A post-baking step was performed at 110° C. for 6 minutes. The SU-8 layer was developed using an XP SU-8 developer from Micro Resist Technology. The SU-8 layer was patterned in order to define areas for the electrolytes and electrodes 107 and for the transport material 102.

An mixture of Poly(ethylene glycol) diacrylate ($M_n$~575 (Aldrich)) and 1% w/w photoinitiator 1-HYDROXYCYCLOHEXYL PHENYL KETONE was deposited, in the one opening in the su8 layer dedicated for 102, by a syringe. Excess material was removed by nitrogen pressure gas so only the hole in the su8 contained the mixture which acts as 102. The device was UV exposed under nitrogen flow by a portable UV-lamp (VL-208 BL, 365 nm light) for 30 s. An approximately 5 mm long and 1 mm wide stripe of FuMA Tech FAB membrane 101 was cut out and laminated on top of 102 and in contact with the 107 element associated with the gate. The lamination was made on a heat plate at 110 C by applying pressure on the stripe from above. The laminated membrane was sealed by PDMS type Sylgard 186, acting as 104, which only left part of the strip exposed to associated 107. The PDMS was cured at 80 C for 1 h.

PREPARATORY EXAMPLE 2

General Procedure for Fabrication of the Ion Gated Ionic Transistor

A circuit according to FIG. 11b with an anionic transistor structure with gate configuration according to FIG. 11c was fabricated in a class 1000 cleanroom using photolithographic techniques and dry etching. In this example conversion elements 107 consisted of PEDOT:PSS electrodes covered by SU8 with openings for electrolytes. A general procedure for fabrication of the ion transport devices is shown below. As substrate, an Orgacon foil (AGFA) was used. Orgacon is a laminate consisting of a first layer of a polyester base and a second layer of PEDOT:PSS.

The Orgacon foil substrate was cleaned by washing in acetone followed by washing in water. The substrate was then baked at 110° C. for 5 min in order to dry the substrate before the etch process step below. The photoresist (S1818 Microposit) was spin coated onto the Orgacon foil substrate. The photoresist was exposed using a mask-aligner (Suss Microtech MA 6/BA 6). Development was done with a Microposit MF319 developer. The non-covered areas of PEDOT:PSS were etched away using a reactive ion plasma consisting of O2 and CF4. This created the basic pattern for the source and target elements 100a, 100b and the electrodes which were part of conversion element 107. The non-etched photoresist was removed using a Microposit remover 1112A. Another layer of photoresist was patterned in order to create opening where PEDOT:PSS was to be over-oxidized to create the control element gate 101. In the opening defined by the patterned photoresist, the PEDOT:PSS was exposed to 1% NaClO solution for 50 seconds. After rinsing in water the photoresist was removed using a Microposit remover 1112A. A layer of SU-8, acting as 104, (Microchem SU-8 2010) was spin-coated onto the patterned PEDOT:PSS. The SU-8 layer was baked by ramping the temperature from 50° C. to 110° C. during 16 minutes. The SU-8 layer was exposed using a mask-aligner (Suss Microtech MA 6/BA 6). A post-baking step was performed at 110° C. for 6 minutes. The SU-8 layer was developed using an XP SU-8 developer from Micro Resist Technology. The SU-8 layer was patterned in order to define areas for the electrolytes and electrodes conversion element 107 and for the transport element material 102.

An mixture of 20% Poly(ethylene glycol) diacrylate ($M_n$~575 (Aldrich)), 78% Poly(ethylene glycol) phenyl ether acrylate ($M_n$·324 (Aldrich)) and 2% w/w photoinitiator 1-HYDROXYCYCLOHEXYL PHENYL KETONE was deposited, filling up the opening in the su8 layer dedicated for the transport element 102, by a Dimatix Material Printer 2800. The device was UV exposed under nitrogen flow by a mask-aligner (Suss Microtech MA 6/BA 6) for 45 s. Next the source and target elements 100a, 100b where created. A protective layer of photoresist (S1818 Microposit) was spin coated and patterned with openings for the source and target elements 100a, 100b. A 10%/w solution of Poly(vinylbenzyl chloride) in toluene was mixed to a 50% molar ratio with trimethylamine solution (~4.2 M in ethanol). After heating the mixture to 65 C for 10 min the reaction product precipitated. The toluene were removed and the precipitate was dissolved in ethanol and mixed with 1,4-Diazabicyclo (2.2.2) octane to a molar ratio of 10%. The solution was spin coated on to the substrate at 1000 rpm and dried in an oven at 110 C for 10 min. A second layer of photoresist (S1818 Microposit) was spin coated and patterned to covered the source and target elements 100a, 100b. The source and target elements 100a, 100b where pattered by dry etch (reactive ion plasma consisting of O2 and CF4) and the remaining photoresist was removed by Microposit remover 1112A. The source and target elements 100a and 100b, the transport element 102 and the control element 101 was sealed by a second layer of Su-8, acting as encapsulation 104.

EXPERIMENT 1

Characterization of Device Fabricated According to Preparatory Example 1

Figure 10A:
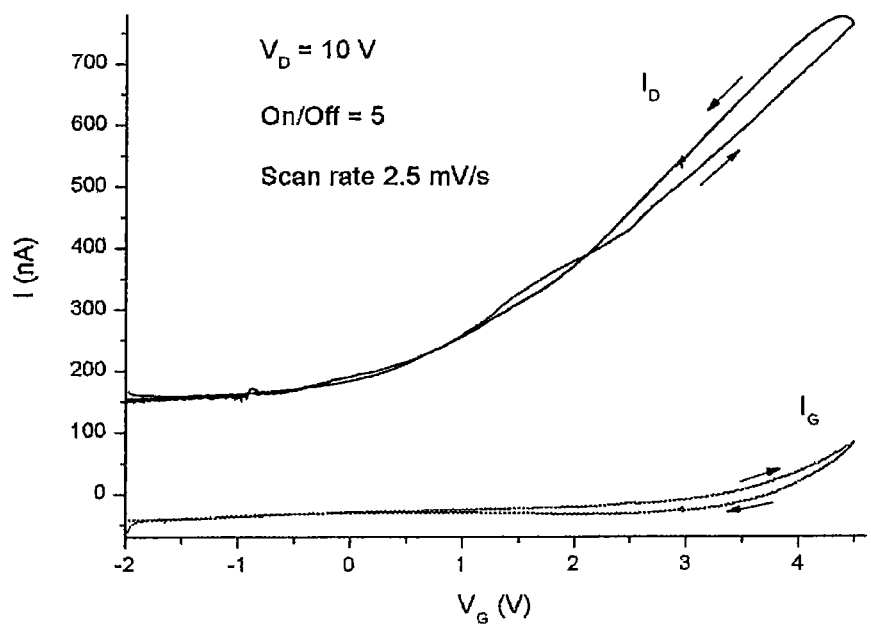
FIGS. 10a-d are graphs illustrating different experimental results of measurements performed on one embodiment of the ion transport device.
Figure 10B:
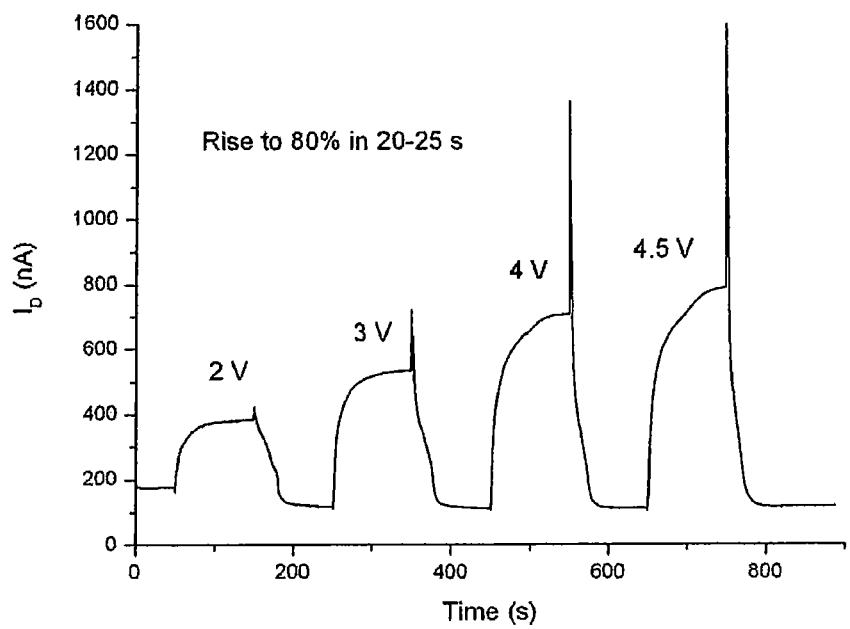

Devices were conditioned in de-ionized water for 24 hours before use. Electrolytes (0.1 M NaCl) was placed on top of the PEDOT:PSS electrodes and created elements 107. Two voltage sources were connected according to FIG. 3b where V1 controlled the gate. In FIG. 10a V2 was set to 10 V while the gate voltage V1 was scanned between −2 and 4.5 V. Id is the current through V2 and Ig is the current through V1. FIG. 10a shows that the device works and that Id can be modulated by V1. In FIG. 10b V1 was set to −2 V when Id was low and to 2 V, 3V, 4 V and 4.5V when Id was high. This shows how V1 can be used to modulate Id.

EXPERIMENT 2

Characterization of Device Fabricated According to Preparatory Example 1

Figure 10C:
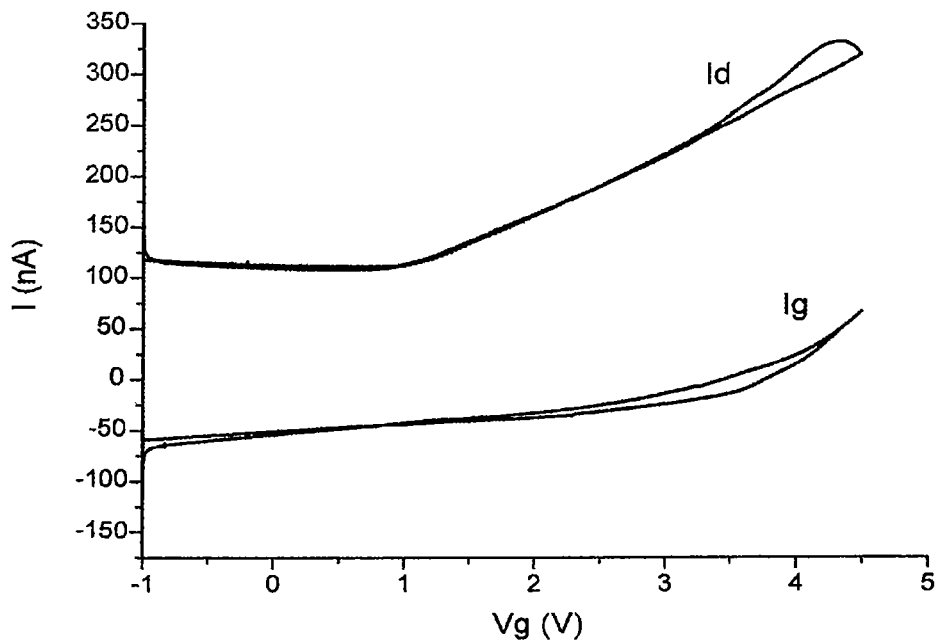

Devices were conditioned in de-ionized water for 24 hours before use. The leftmost element 107 contained 0.1 M AChCl (acetylcholine chloride) and the other 107 contained 0.1 M NaCl. Two voltage sources were connected according to FIG. 3b where V1 controlled the gate. In FIG. 10c V2 was set to 10 V while the gate voltage V1 was scanned between −1 and 4.5 V. Id is the current through V2 and Ig is the current through V1. FIG. 10c shows that ACh can be transported through the device and that Id can be modulated by V1.

EXPERIMENT 3

Cell Experiment with Device Fabricated According to Preparatory Example 1

Figure 10D:
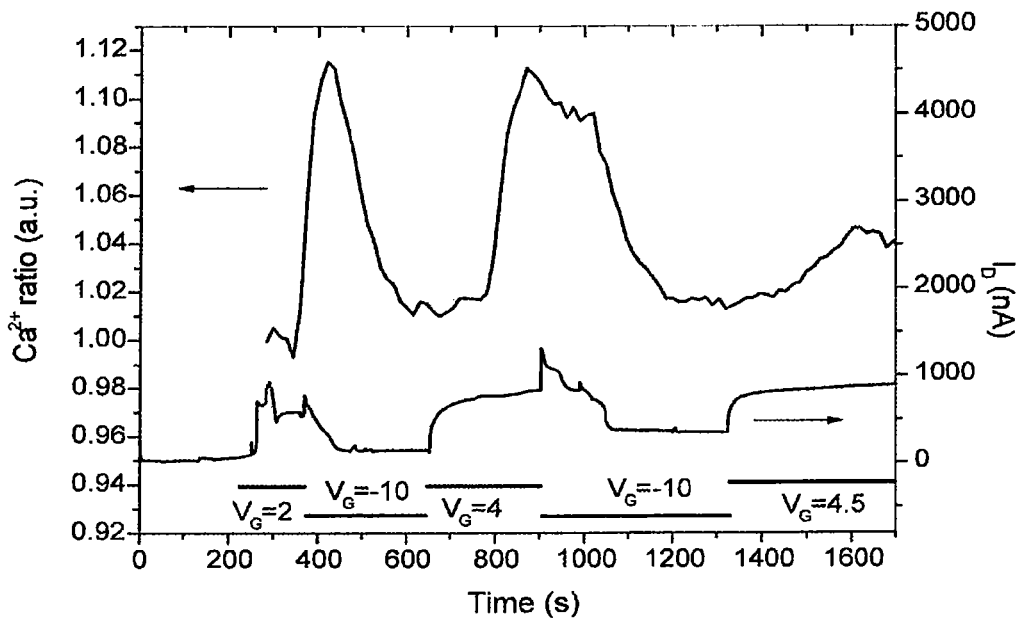

Devices were conditioned in de-ionized water for 24 hours before use. The leftmost element 107 contained a water solution of 0.1 mM AChCl and 0.1 M NaCl, the 107 connected to the gate contained 0.1 M NaCl and the rightmost 107 contained cell medium with SH-SY5Y nerve cells cultured on top of the PEDOT:PSS electrode. The cells were loaded with the ratiometric $Ca^{2+}$ fluorophore Fura 2-AM so their intracellular calcium level could be recorded by microscopy-based real-time imaging (Nikon Eclipse 80i with a 40×/0.80 epifluorescence objective). Two voltage sources were connected according to FIG. 3b where V1 controlled the gate. In FIG. 10c V2 was set to 10 V while the gate voltage V1 was varied according to FIG. 10d. Id is the current through V2. FIG. 10d shows that ACh can be transported through the device and that Id can be modulated by V1. FIG. 10d also shows that the cell response (intracellular Ca2+) can be modulated by the device (left axis).

The present invention is applicable for delivery of ions to biological systems in vitro and/or in vivo. Delivery of ions to regulate protein/DNA/macromolecule functionality (e.g. fibril formation). Delivery of ions to cause/regulate chemical reactions. Delivery of ions to trigger release of molecules/ macromolecules from a responsive gel containing said molecules/macromolecules (e.g. pH sensitive gel like chitosan). Delivery of ions to break a sealing of a compartment to trigger release of molecules/macromolecules.

EXPERIMENT 4

Characterization of Device Fabricated According to Preparatory Example 2

Figure 14A:
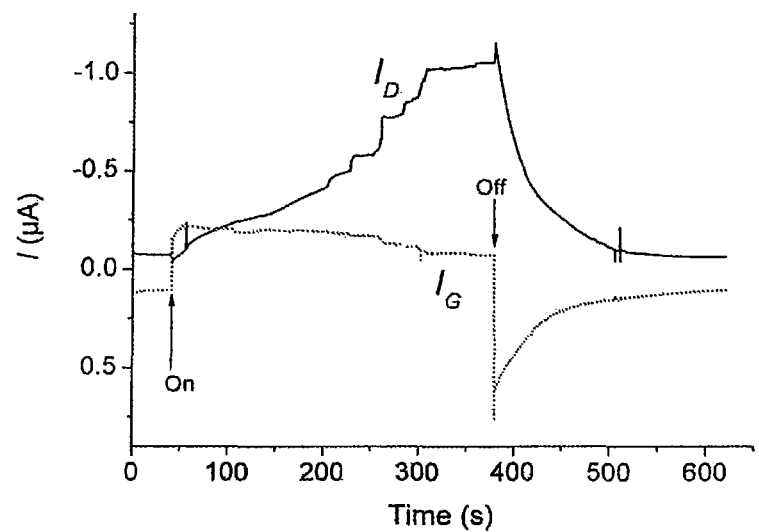
FIGS. 14a and 14b are graphs illustrating different experimental results of measurements performed on one embodiment of the ion transport device

Devices were conditioned in 0.1 M NaCl (aq) solution for 24 hours before use. Electrolytes (0.1 M NaCl) was placed on top of the PEDOT:PSS electrodes and created conversion elements 107. Two voltage sources were connected according to FIG. 11b where V1 controlled the gate. In FIG. 11b V2 was set to −10 V while the gate voltage V1 was switched between 2 V (off) and −3 V (on). Id is the current through V2 and Ig is the current through V1. FIG. 14a shows that the device works and that Id can be modulated by V1. In FIG. 14a V1 was set to −2 V to set the device in the off state with low Id. V1 was set to −3 to set the device in the on state with high Id.

EXPERIMENT 5

Characterization of Device Fabricated According to Preparatory Example 2

Figure 14B:
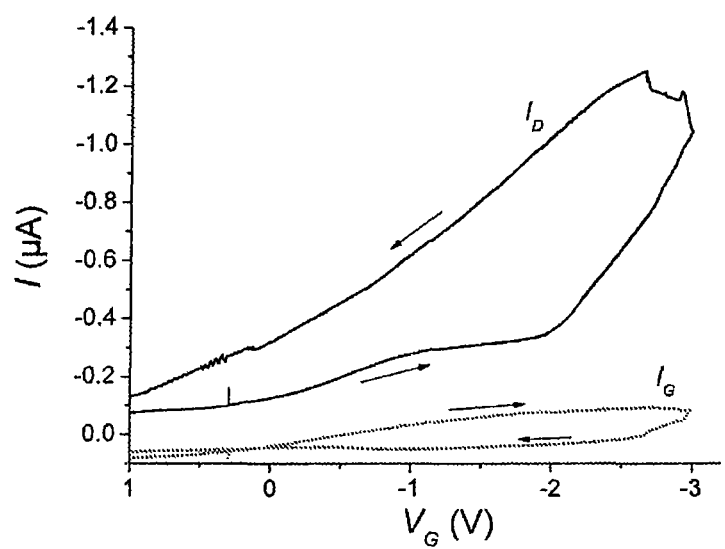

Devices were conditioned in 0.1 M NaCl (aq) solution for 24 hours before use. Electrolytes (0.1 M NaCl) was placed on top of the PEDOT:PSS electrodes and created conversion elements 107. Two voltage sources were connected according to FIG. 11b where V1 controlled the gate. In FIG. 11b V2 was set to −10 V while the gate voltage V1 was scanned between 1 and −3 V. Id is the current through V2 and Ig is the current through V1. FIG. 14b shows that the device works and that Id can be modulated by V1.

The invention has mainly been described above with reference to a number of explicitly disclosed embodiments. However, as is readily appreciated by a person skilled in the art, other embodiments than the ones disclosed above are equally possible within the scope of the invention, as defined by the appended patent claims.

The invention claimed is:

1. An ionic transistor device for controlled transport of ions comprising:
a first source element arranged to receive ions of a first class from an ion source,
a first target element arranged to release ions of said first class to an ion target, wherein each of said first source element and said first target element comprises an ion selective electrochemically active material which conducts said first class of ions,
a first control element corresponding to the gate of said ionic transistor device, the first control element comprising ion selective electrochemically active material which conducts a second class of ions, wherein said first class of ions is one of cations and anions, and said second class of ions is the other one of cations and anions, and
a first ion transport element arranged in direct ionic contact with all of said first source element, said first target element and said first control element,
wherein said first control element is arranged to receive a first electrochemical potential which increases the concentration of ions of said second class in said ion transport element, and wherein said first ion transport element is further arranged to receive ions of said first class from said first source element in response to said increased concentration of ions of said second class, to release ions of said first class to said first target element in response to a second electrochemical potential difference provided across said ion transport element and said first source element, and to provide an ionic connection for said ions of said first class between said first source element and said first target element.

2. The device in accordance with claim 1, wherein said first ion transport element comprises an excess of fixed ions of said second class, such that a predetermined increase of the said second electrochemical potential applied to said ion transport element provides an increased conductivity of ions of said first class in said ion transport element.

3. The device in accordance with claim 1, further comprising a second ion transport element,
wherein said first control element is arranged to receive ions of said second class from a control ion source,
wherein said first ion transport element is arranged to receive ions of said second class from said first control element in response to the first electrochemical potential difference provided across said ion transport element and said first control element, which received ions raises the concentration of ions of said second class in said first ion transport element at least until said applied first electrochemical potential difference is substantially altered, and
wherein said second ion transport element is arranged to release ions of said second class to said first control element in response to a third electrochemical potential difference provided across said first ion transport element and said first control element, so as to enable a control of the transport of ions of said first class between said first source element and said first target element by means of an electrochemical potential applied across said first ion transport element and said first control element.

4. The device according to claim 1, wherein said first source element, said first target element and said first control element are arranged as layers carried by a substrate, wherein said layers preferably are substantially parallel.

5. The device according to claim 1, wherein the first ion transport element covers at least a respective portion of said first source element, said first target element and said first control element, wherein the side of said first control element and the side of said first target element, which are covered by said ion transport element, both faces in the same direction.

6. The device according to claim 1, wherein said first control element, said first source element and said first target element are spatially separated from each other by means of an intermediate member, wherein said intermediate member preferably comprises at least a portion of said ion transport element.

7. The device according to claim 1, wherein one, two, three or four of said first source element, said first target element, said first control element and said ion transport element comprises a solid or semi-solid material, which is/are directly or indirectly attached to a support.

8. The device according to claim 1, further comprising a second control element, arranged in ionic contact with and spatially separated from said first control element.

9. A device according to claim 1, further comprising:
a source receptacle for receiving a source electrolyte,
a target receptacle for receiving a target electrolyte,
a control receptacle for receiving a control electrolyte,
wherein said source and target electrolytes comprises ions of said first class, and said control electrolyte comprises ions of said second class,
wherein said first source element of said ion transport device is ionically connected to said source receptacle, said first target element of said ion transport device is connected to said target receptacle, and said first control element of said ion transport device is ionically connected to said control receptacle, means for providing a first electrochemical potential difference between said control receptacle and said first ion transport element of said ion transport device for enabling transport of ions of said second class from said control receptacle to said first ion transport element of said ion transport device, means for providing a second electrochemical potential difference between said source receptacle and said target receptacle for enabling transport of ions of said first class from said source receptacle to said target receptacle, means for providing a third electrochemical potential difference between said control receptacle and said first ion transport element of said ion transport device for enabling transport of ions of said second class from said first ion transport element to said control receptacle.

10. The device according to claim 9, wherein said means for providing an electrochemical potential difference between a pair of elements selected from a group consisting of said first source element, said first target element and said first control element, comprises:
  a first electrode arranged to receive a predetermined electric potential, and
  a first electrolyte, which electrolyte ionically connects said first electrode to a first one of said pair of elements,
  a second electrode arranged to receive a predetermined electric potential, and
  a second electrolyte, which electrolyte ionically connects said second electrode to a second one of said pair of elements,
  wherein said electrochemical potential difference is applicable to said pair of elements by providing a predetermined electric potential difference to said first and second electrodes.

11. A device according to claim 1, further comprising:
a second device, comprising:
  a first source element arranged to receive ions of a first class from an ion source,
  a first target element arranged to release ions of said first class to an ion target, wherein each of said first source element and said first target element comprises an ion selective material, which conducts said first class of ions,
  first control element comprising ion selective material, which conducts a second class of ions,
    wherein said first class is one of cations and anions, and said second class is the other one of cations and anions,
  a first ion transport element arranged in direct ionic contact with all of said first source element, said first target element and said first control element,
    wherein said first control element is arranged to receive a first electrochemical potential which increases the concentration of ions of said second class in said ion transport element, and
    wherein said first ion transport element is further arranged to receive ions of said first class from said first source element in response to said increased concentration of ions of said second class, to release ions of said first class to said first target element, in response to a second electrochemical potential difference provided across said ion transport element and said first source element, and to provide an ionic connection for said ions of said first class between said first source element and said first target element said device for controlled transport of ions and said second device being arranged in series with each other, wherein an ionic connection is provided between the first target element of said device for controlled transport of ions and the first source element of said second device, such that ions are transportable from the first source element of said device for controlled transport of ions via the ionic connection to the first target element of said second device, at least after a first electrochemical potential difference has been provided between the control element and the ion transport element of said device for controlled transport of ions and said second devices, respectively.

12. An ionic transistor device for controlled transport of ions comprising:
  a first source element arranged to receive ions of a first class from an ion source, and
  a first target element arranged to release ions of said first class to an ion target, wherein each of said first source element and said first target element comprises an ion selective electrochemically active material which when subjected to an electrochemical potential selectively conducts said first class of ions,
  a first control element corresponding to the gate of said ionic transistor device, the first control element comprising ion selective electrochemically active material which conducts a second class of ions, wherein said first class of ions is one of cations and anions, and said second class of ions is the other one of cations and anions, and
  a first ion transport element arranged to receive ions of said second class from said first control element in response to a first electrochemical potential difference provided across said first ion transport element and said first control element, which received ions of said second class increases the concentration of ions of said second class in said first ion transport element at least until said applied potential difference is substantially altered;
  arranged to receive ions of said first class from said first source element in response to said increased concentration of ions of said second class in said first ion transport element, to release ions of said first class to said first target element in response to a second electrochemical potential difference provided across said first ion transport element and said first source element, and to provide an ionic connection for ions of said first class between said first source element and said first target element; and
  arranged to release ions of said second class to said first control element in response to a third electrochemical potential difference provided across said first ion transport element and said first control element, so as to enable a control of the transport of ions of said first class between said first source element and said first target element by means of an electrochemical potential applied across said first ion transport element and said first control element.

13. The device according to claim 12, wherein said first ion transport element is arranged in ionic contact with all of said first source element, said first target element and said first control element.

14. The device according to claim 12, wherein said first control element is arranged to receive ions of said second class from an ion source.

15. The device according to claim 12, wherein said first source element, said first target element and said first control element are arranged as layers carried by a substrate, wherein said layers preferably are substantially parallel.

16. The device according to claim 12, wherein the first ion transport element covers at least a respective portion of said first source element, said first target element and said first control element, wherein the side of said first control element and the side of said first target element, which are covered by said ion transport element, faces in opposite directions.

17. The device according to claim 12, wherein said first control element, said first source element and said first target element are spatially separated from each other by means of an intermediate member, wherein said intermediate member preferably comprises at least a portion of said ion transport element.

18. The device according to claim 12, wherein one, two, three or four of said first source element, said first target element, said first control element and said ion transport element comprises a solid or semi-solid material, which is/are directly or indirectly attached to a support.

19. The device according to claim 12, further comprising a second control element, arranged in ionic contact with and spatially separated from said first control element.

20. A method for the controlled transport of ions, comprising:
providing an ionic transistor device comprising:
- a first source element arranged to receive ions of a first class from an ion source,
- a first target element arranged to release ions of said first class to an ion target, wherein each of said first source element and said first target element comprises an ion selective electrochemically active material which conducts said first class of ions,
- a first control element corresponding to the gate of said ionic transistor device, the first control element comprising ion selective electrochemically active material which conducts a second class of ions, wherein said first class of ions is one of cations and anions, and said second class of ions is the other one of cations and anions, and
- a first ion transport element arranged in direct ionic contact with all of said first source element, said first target element and said first control element,
wherein said first control element is arranged to receive a first electrochemical potential which increases the concentration of ions of said second class in said ion transport element, and
wherein said first ion transport element is further arranged to receive ions of said first class from said first source element in response to said increased concentration of ions of said second class, to release ions of said first class to said first target element, in response to a second electrochemical potential difference provided across said ion transport element and said first source element, and to provide an ionic connection for said ions of said first class between first source element and said first target element
providing a source electrolyte;
providing a target electrolyte;
bringing said first source element of the device in contact with the source electrolyte, and bringing the first target element of the device in contact with the target electrolyte;
providing a first control electrochemical potential between said source element and said target element of the device, and
providing a first transport electrochemical potential between said first control element and the ion transport element of said device to effectuate a change in the ion transport rate of said device.

\* \* \* \* \*